US012704518B2

(12) United States Patent
Edelmann et al.

(10) Patent No.: US 12,704,518 B2
(45) Date of Patent: Aug. 11, 2026

(54) METHOD FOR THE DETERMINATION OF HYDROLYTIC ACTIVITY

(71) Applicant: Hoffmann-La Roche Inc., Little Falls, NJ (US)

(72) Inventors: Franziska Edelmann, Wolfratshausen (DE); Roberto Falkenstein, Munich (DE); Tobias Graf, Penzberg (DE); Sanjay Gupta, Munich (DE); Lars Hillringhaus, Königsdorf-Schönrain (DE); Tarik Ali Khan, Basel (CH); Michael Leiss, Schlehdorf (DE); Thomas Meier, Munich (DE); Michael Wiedmann, Penzberg (DE)

(73) Assignee: Hoffmann-La Roche Inc., Branchburg, NJ (US)

( * ) Notice: Subject to any disclaimer, the term of this patent is extended or adjusted under 35 U.S.C. 154(b) by 830 days.

(21) Appl. No.: 18/067,459

(22) Filed: Dec. 16, 2022

(65) Prior Publication Data

US 2023/0358748 A1 Nov. 9, 2023

(30) Foreign Application Priority Data

Dec. 21, 2021 (EP) .................................... 21216295

(51) Int. Cl.
*G01N 33/573* (2006.01)
*C12Q 1/44* (2006.01)
*G01N 1/44* (2006.01)

(52) U.S. Cl.
CPC ............. *G01N 33/573* (2013.01); *C12Q 1/44* (2013.01); *G01N 1/44* (2013.01); *G01N 2333/918* (2013.01)

(58) Field of Classification Search
CPC .. G01N 33/573; G01N 1/44; G01N 2333/918; C12Q 1/44; C12Q 1/34
See application file for complete search history.

(56) References Cited

U.S. PATENT DOCUMENTS

| | | | |
|---|---|---|---|
| 4,676,980 A | 6/1987 | Segal et al. |
| 4,816,567 A | 3/1989 | Cabilly et al. |
| 5,731,168 A | 3/1998 | Carter et al. |
| 2002/0004587 A1 | 1/2002 | Miller et al. |
| 2008/0069820 A1 | 3/2008 | Fuh et al. |

FOREIGN PATENT DOCUMENTS

| | | | |
|---|---|---|---|
| EP | 0061888 A2 | 10/1982 |
| EP | 0580979 A2 | 2/1994 |
| WO | 90/005301 A1 | 5/1990 |
| WO | 92/14138 A1 | 8/1992 |
| WO | 93/08829 A1 | 5/1993 |
| WO | 96/027011 A1 | 9/1996 |
| WO | 98/50431 A2 | 11/1998 |
| WO | 98/50431 A3 | 11/1998 |
| WO | 01/73442 A1 | 10/2001 |
| WO | 01/077342 A1 | 10/2001 |
| WO | 2008/024715 A2 | 2/2008 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 90/11511 A1 | 10/2009 |
| WO | 2010/112193 A1 | 10/2010 |
| WO | 2010/115589 A1 | 10/2010 |
| WO | 2010/136172 A1 | 12/2010 |
| WO | 2010/145793 A1 | 12/2010 |
| WO | 2012/163520 A1 | 12/2012 |
| WO | 2013/026831 A1 | 2/2013 |
| WO | 2015/095539 A1 | 6/2015 |
| WO | 2015/150447 A1 | 10/2015 |
| WO | 2016/016299 A1 | 2/2016 |
| WO | 2016/172485 A2 | 10/2016 |
| WO | 2021/050585 A1 | 3/2021 |
| WO | 2010/145792 A1 | 12/2023 |

OTHER PUBLICATIONS

Lingeman et al., "Rapid, Sensitive and Specific Derivatization Methods With 9-(Hydroxymethyl)Anthracene for the Fluorimetric Detection of Carboxylic Acids Prior to Reversed-Phase Highperformance Liquid Chromatographic Separation" Journal of Chromatography 290:215-222 (1984).
Kishore et al., "The Degradation of Polysorbates 20 and 80 and its Potential Impact on the Stability of Biotherapeutics" Pharmceutical Research 28:1194-1210 (Mar. 3, 2011).
EnzyChromTM Free Fatty Acid Assay Kit (EFFA-100) (Quantitative Colorimetric/Fluorimetric Fatty Acid Determination; BioAssay Systems;2014).

(Continued)

*Primary Examiner* — Shafiqul Haq
(74) *Attorney, Agent, or Firm* — Hoffmann-La Roche Inc.

(57) ABSTRACT

Herein is reported a method for determining the presence of hydrolase activity in a sample by incubating the sample in a buffered solution, which comprises an artificial hydrolase substrate that comprises an ester bond covalently linking an alcohol residue, which is conjugated to a label for removal, and a carboxylic acid residue, which is conjugated to a capture and detection label, as well as bovine serum albumin, and thereafter determining or quantifying, respectively, the released carboxylic acid in the free alcohol depleted incubation mixture.

16 Claims, 13 Drawing Sheets

Specification includes a Sequence Listing.

(56) References Cited

OTHER PUBLICATIONS

Aslam, M. et al. Bioconjugation: Protein Coupling Techniques for the Biomedical Sciences "Chapter 2: The Functional Chemistry of Proteins and Protein Coupling" Aslam, M, & Dent, A., eds, First edition, London, GB:MacMillian Reference Limited,:50-100 (Jan. 1, 1998).
Atwell, S., et al., "Stable heterodimers from remodeling the domain interface of a homodimer using a phage display library" J Mol Biol 270(1):26-35 (Jul. 4, 1997).
Ayorinde, F.O. et al., "Analysis of some commercial polysorbate formulations using matrix-assisted laser desorption/ionization time-of-flight mass spectrometry" Repid Comm. Mass Spectrom 14(22):2116-2124 (Nov. 2000).
Bhargava, A. C. et al., "High-Throughput, Fluorescence-Based Esterase Activity Assay for Assessing Polysorbate Degradation Risk during Biopharmaceutical Development" Pharm. Res. 38:397-413 (Mar. 2, 2021).
Brandner, J.D. et al., "The Composition of NF-Defined Emulsifiers: Sorbitan Monolaurate, Monopalmitate, Monostearate, Monooleate, Polysorbate 20, Polysorbate 40, Polysorbate 60, and Polysorbate 80" Drug Devel. Ind. Pharm. 24(11):1049-1054 (1998).
Brennan, M., et al., "Preparation of Bispecific Antibodies By Chemical Recombination of Monoclonal Immunoglobulin G1 Fragments" Science 229:81-83 (Jul. 5, 1985).
Bresolin, I.R.A.P. et al., "Hydrophobic interaction chromatography as polishing step enables obtaining ultra-pure recombinant antibodies" J. Biotechnol. 324(100020):1-7 (May 19, 2020).
Butler, J.E. et al., "Solid Supports in Enzyme-Linked Immunosorbent Assay and Other Solid-Phase Immunoassays" Methods 22:4-23 (2000).
Cao, X et al., "Free Fatty Acid Particles in Protein Formulations, Part 1: Microspectroscopic Identification" J. Pharm. Sci. 104:433-446 (2015).
Cheng, Y. et al., "A Rapid High-Sensitivity ReversedePhase Ultra High Performance Liquid Chromatography Mass Spectrometry Method for Assessing Polysorbate 20 Degradation in Protein Therapeutics" J. Pharm. Sci. 108:2880-2886 (2019).
Chiu, J. et al., "Knockout of a Difficult-to-Remove CHO Host Cell Protein, Lipoprotein Lipase, for Improved Polysorbate Stability in Monoclonal Antibody Formulations" Biotechnol. Bioeng. 114:1006-1015 (2017).
Chothia et al., "Canonical structures for the hypervariable regions of immunoglobulins" J Mol Biol 196:901-917 (1987).
Dahotre, S. et al., "Novel markers to track oxidative polysorbate degradation in pharmaceutical formulations" J. Pharm. Biomed. Anal. 157:201-207 ( 2018).
Dixit, N. et al., "Residual Host Cell Protein Promotes Polysorbate 20 Degradation in a Sulfatase Drug Product Leading to Free Fatty Acid Particles" J. Pharm. Sci. 105:1657-1666 (2016).
Doshi, N. et al., "Evaluation of Super Refined™ Polysorbate 20 With Respect to Polysorbate Degradation, Particle Formation and Protein Stability" J. Pharm. Sci. 109:2986-2995 (2000).
Doshi, N. et al., "Understanding Particle Formation: Solubility of Free Fatty Acids as Polysorbate 20 Degradation Byproducts in Therapeutic Monoclonal Antibody Formulations" Mol. Pharm. 12:3792-3804 (2015).
Dwivedi, M. et al., "Polysorbate degradation in biotherapeutic formulations: Identification and discussion of current root causes" Int. J. Pharm. 552:422-436 (2018).
Flatman, S., et al., "Process analytics for purification of monoclonal antibodies" J Chromatogr 848(1):79-87 (Mar. 15, 2007).
Frison-Norrie, S. et al., "Investigating the molecular heterogeneity of polysorbate emulsifiers by MALDI-TOF MS" J. Agric. Food Chem. 49(7):3335-3340 (2001).
Glucklich, N. et al., "Assessing the polysorbate degradation fingerprints and kinetics of lipases—how the activity of polysorbate degrading hydrolases is influenced by the assay and assay conditions" Eur J Pharm. Sci. 166(105980):1-12 (Aug. 20, 2021).
Graf, T. et al., "Controlled polysorbate 20 hydrolysis—A new approach to assess the impact of polysorbate 20 degradation on biopharmaceutical product quality in shortened time" Eur J Pharm. Biopharm. 152:318-326 (2020).
Graham, F., et al., "Characteristics of a Human Cell Line Transformed by DNA form Human Adenovirus Type 5" J Gen Virol 36(1):59 (Jul. 1, 1977).
Hage, D.S., "Immunoassays" Anal Chem 71(12):294R-304R (May 20, 1999).
Hall, T. et al., "Polysorbates 20 and 80 Degradation by Group XV Lysosomal Phospholipase A2 Isomer X1 in Monoclonal Antibody Formulations" J. Pharm. Sci. 105:1633-1642 ( 2016).
Hoffmann and Stroobant et al. Mass spectrometry: principles and applications Bruxellas Belgica,West Sussex: John Wiley & Sons, vol. 1(2) (2007).
Holliger, P., et al., "Diabodies: Small Bivalent and Bispecific Antibody Fragments" PNAS USA 90(14):6444-6448 (Jul. 15, 1993).
Honemann, M.N. et al., "Monitoring polysorbate hydrolysis in biopharmaceuticals using a QC-ready free fatty acid quantification method" J. Chromatogr. B 1116:1-8 (2019).
Horvath, C. and Melander, J. et al., "Liquid Chromatography with Hydrocarbonaceous Bonded Phases; Theory and Practice of Reversed Phase Chromatography" J. Chrom. Sci. 15(9):393-404 ( 1977).
Hweitt, D. et al., "Mixed-mode and reversed-phase liquid chromatography-tandem mass spectrometry methodologies to study composition and base hydrolysis of polysorbate 20 and 80" J. Chrom. A 1218:2138-2145 (2011).
International Search Report with Written Opinion for PCT/E P2022/083610 mailed Feb. 10, 2023, pp. 1-15.
Jahn, M. et al., "Measuring Lipolytic Activity to Support Process Improvements to Manage Lipase-Mediated Polysorbate Degradation" Pharm. Res. 37(118):1-13 (Jun. 3, 2020).
Kabat, EA et al. Sequences of Proteins of Immunological Interest Fifth edition, NIH Publication,:91-3242 ( 1991).
Keratichewanun, S. et al., "An Investigation of Nifedipine Miscibility in Solid Dispersions Using Raman Spectroscopy" Pharm. Res. 32:2458-2473 (2015).
Khan, F. I. et al., "The Lid Domain in Lipases: Structural and Functional Determinant of Enzymatic Properties" Front. Bioeng. Biotechnol. 5(Article 16):1-13 (Mar. 9, 2017).
Kishore, R.S. et al., "Degradation of Polysorbates 20 and 80: Studies on Thermal Autoxidation and Hydrolysis" J .Pharm. Sci 100(2):721-731 ( 2011).
Klein, C. et al., "The use of CrossMAb technology for the generation of bi- and multispecific antibodies" MABS 8(6):1010-1020 (Aug. 31, 2016).
Kostelny, S., et al., "Formation of a bispecific antibody by the use of leucine zippers" J Immunol 148(5):1547-1553 (Mar. 1, 1992).
Labrenz, S.R. et al., "Ester Hydrolysis of Polysorbate 80 in mAb Drug Product: Evidence in Support of the Hypothesized Risk After the Observation of Visible Particulate in mAb Formulations" J. Pharm. Sci. 103:2268-2277 (2014).
Lanza, A., et al., "Using the Cre/lox system for targeted integration into the human genome: loxFAS-loxP pairing and delayed introduction of Cre DNA improve gene swapping efficiency" Biotechnol J 7(7):898-908 (Jul. 1, 2012).
Li, X. et al., "Profiling Active Enzymes for Polysorbate Degradation in Biotherapeutics by Activity-Based Protein Profiling" Anal. Chem. :8161-8169 (May 25, 2021).
Li, X. et al., "The measurement and 1-17 control of high-risk host cell proteins for polysorbate degradation in biologics formulation" Antibody Ther. 5(1):42-54 (Jan. 15, 2022).
Li, Y. et al., "Characterization and Stability Study of Polysorbate 20 in Therapeutic Monoclonal Antibody Formulation by Multidimensional UltrahighPerformance Liquid Chromatography-Charged Aerosol Detection-Mass Spectrometry" Anal. Chem. 86:5150-5157 ( 2014).
Lippold, S., et al., "Impact of mono- and poly-ester fractions on polysorbate quantitation using mixed-mode HPLC-CAD/ELSD and the fluorescence micelle assay" J. Pharm. Biomed. Anal. 132:24-34 ( 2017).

(56) References Cited

OTHER PUBLICATIONS

Lu, B., et al., "Tutorial review. Oriented immobilization of antibodies and its applications in immunoassays and immunosensors" Analyst 121(3):29R-32R (Mar. 1, 1996).
Maccallum, R., et al., "Antibody-antigen Interactions: Contact Analysis and Binding Site Topography" J Mol Biol 262:732-745 (Oct. 11, 1996).
Martin, C., et al., "Peer Reviewed: Nanomaterials in Analytical Chemistry" ACS Anal Chem News & Features 70(9):322A-327A (May 1, 1998).
Martos. A., et al., "Trends on Analytical Characterization of Polysorbates and Their Degradation Products in Biopharmaceutical Formulations" J. Pharm. Sci. 106:1722-1735 (2017).
Mather, J., et al., "Culture of Testicular Cells in Hormone-Supplemented Serum-Free Medium" Ann NY Acad Sci 383:44-68 ( 1982).
Mather, J., "Establishment and Characterization of Two Distinct Mouse Testicular Epithelial Cell Lines" Biol Reprod 23:243-252 ( 1980).
Merchant et al., "An efficient route to human bispecific IgG" Nat Biotechnol 16(7):677-681 (Jul. 1, 1998).
Milstein, C., et al., "Hybrid hybridomas and their use in immunohistochemistry" Nature 305(5934):537-540 (Oct. 6, 1983).
Pilely, K., et al., "A novel approach to evaluate ELISA antibody coverage of host cell proteins-combining ELISA-based immunocapture and mass spectrometry" Biotechnol. Prog. E2983:1-12 (Feb. 17, 2020).
Ransac, S., et al., "The Kinetics, Specificities and Structural Features of Lipases" Molecular Dynamics of Biomembrances H96:265-304 (1996).
Review, C.D.I., "Final Report on the Safety Assessment of Polysorbates 20, 21, 40, 60, 61, 65, 80, 81, and 85" J.Am. Coll. Toxicol. 3(5):1-82 (1984).
Ridgway et al., "Knobs-into-holes' engineering of antibody C $_{H}$3 domains for heavy chain heterodimerization" Protein Eng 9(7):617-621 1996).
Saggu, M., et al., "Identification of Subvisible Particles in Biopharmaceutical Formulations Using Raman Spectroscopy Provides Insight into Polysorbate 20 Degradation Pathway" Pharm. Res. 32:2877-2888 (2015).
Schaefer, W., et al., "Immunoglobulin domain crossover as a generic approach for the production of bispecific IgG antibodies" PNAS USA 108(27):11187-11192 (Jul. 5, 2011).
Scheib, H. et al., "Untersuchungen zur Regio- und Stereoselektivität von Lipasen durch computergestütztes Molecular Modeling und molekularbiologische Methoden" Zusammenfassung (1999).
Sekhon, B.S. et al., "Surfactants: Pharmaceutical and Medicinal Aspects" JPTRM 1 (May 2013).
Shukla, A. et al., "Host cell protein clearance during protein A chromatography: development of an improved column wash step" Biotechnol Prog 24(5):1115-1121 (Oct. 14, 2008).
Siska, C.C. et al., "Free Fatty Acid Particles in Protein Formulations, Part 2: Contribution of Polysorbate Raw Material" J. Pharm. Sci. 104:447-456 (2015).
Thompson, J.H. et al., "Improved detection of host cell proteins (HCPs) in a mammalian cell-derived antibody drug using liquid chromatography/mass spectrometry in conjunction with an HCP-enrichment strategy" Rapid Comm. Mass Spectrom. 28(8):855-860 (2014).
Tomlinson, A. et al., "Polysorbate 20 Degradation in Biopharmaceutical Formulations: Quantification of Free Fatty Acids, Characterization of Particulates, and Insights into the Degradation Mechanism" Mol. Pharm. 12:3805-3815 (2015).
Traunecker, A., et al., "Bispecific single chain molecules (Janusins) target cytotoxic lymphocytes on HIV infected cells" EMBO J 10(12):3655-3659 (Dec. 10, 1991).
Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).
Urlaub, G., et al., "Isolation of chinese hamster cell mutants deficient in dihydrofolate reductase activity" PNAS US 77(7):4216-4220 (Jul. 1, 1980).
Valente, K., et al., "Expression of difficult-to-remove host cell protein impurities during extended Chinese hamster ovary cell culture and their impact on continuous bioprocessing" Biotechnol Bioeng 112(6):1232-1242 (Jun. 1, 2015).
Verger, R. et al., "Interfacial activation of lipases: facts and artifacts" Trends Biotechnol. 15(1):33-38 (1997).
Vu Dang, H. et al., "Composition analysis of two batches of polysorbate 60 using MS and NMR techniques" J. Pharm. Biomed. Anal. 40:1155-65 (2006).
Wang, X. et al., "Host cell proteins in biologics development: Identification, quantitation and risk assessment" Biotechnol Bioeng 103(3):446-458 (Jun. 15, 2009).
Wilchek, M., et al. Methods in Enzymology "Chapter 54: Avidin-biotin Mediated Immunoassays: Overview" Wilchek, M. & Bayer, E. eds., New York, NY USA: Academic Press, Inc.—Elsevier BV., vol. 184:467-469 (1990).
Woelfel, J. et al., "CAP-T cell expression system: a novel rapid and versatile human cell expression system for fast and high yield transient protein expression." BMC Proc. 5(P133):1-2 (2011).
Wong, E., et al., "Reproducible doxycycline-inducible transgene expression at specific loci generated by Cre-recombinase mediated cassette exchange" Nucleic Acids Res 33(17):e147 (1-13) (Oct. 4, 2005).
Yazaki, P. et al., "Expression of recombinant antibodies in mammalian cell lines" Methods Molec. Biol. 248:255-268 (2004).
Zhang, L. et al., "Dual Effect of Histidine on Polysorbate 20 Stability: Mechanistic Studies" Pharm. Res. 35(33):1-18 (2018).
Zhang, R. et al., "Analysis of Polysorbate 80 and its Related Compounds by RP-HPLC with ELSD and MS Detection" J. Chrom. Sci. 50:598-607 (2012).
Zhang, S. et al., "Monitoring polysorbate hydrolysis in therapeutic proteins using an ultrasensitive extraction-free fatty acid quantitation method" Anal. Biochem. 637(114472):1-9 (Nov. 18, 2021).
Zhang, S. et al., "Putative Phospholipase B-Like 2 is Not Responsible for Polysorbate Degradation in Monoclonal Antibody Drug Products" J. Pharm. Sci. 109:2710-2718 (2020).

R1... Substrate depletion, e.g Biotin
R2... Epitope 1 or direct bead binding e.g LNA
R3... Epitope 2 e.g Dig or direct Ru-lable

B

| TERM | ESTIMATE |
|---|---|
| BSA (0,0,1) | 437,8500 |
| NaCl (25,1000) | -195,4500 |
| BSA*NaCl | -185,3250 |
| BUFFER CONC. (20,50) | 48,9450 |
| BUFFER (HEPES) | -35,5850 |
| BIVALENT CONC. (5,10) | -23,9350 |
| pH (7,8) | 21,9150 |
| BIVALENT (CaCl2) | 14,1650 |
| TEMPERATURE (25,37) | 11,2150 |
| METHIONINE (0,7) | 9,0150 |

| TERM | ESTIMATE |
|---|---|
| BUFFER CONC. (20,50) | 101,4000 |
| BSA* (0,0,1) | 98,7500 |
| BSA*NaCl | -61,2500 |
| NaCl (25,1000) | -49,2000 |
| pH (5,6) | -39,3500 |
| TEMPERATURE (25,37) | -37,8500 |
| METHIONINE (0,7) | -36,1000 |
| BIVALENT (CaCl2) | -25,6500 |
| BUFFER (CITRATE) | 24,2000 |
| BIVALENT CONC. (5,10) | -19,5500 |

METHOD FOR THE DETERMINATION OF HYDROLYTIC ACTIVITY

CROSS-REFERENCE TO RELATED APPLICATIONS

This application claims priority to European Patent Application No. 21216295.2, filed Dec. 21, 2021, which is incorporated herein by reference in its entirety.

SEQUENCE LISTING

This application contains a Sequence Listing which has been submitted electronically in XML format and is hereby incorporated by reference in its entirety. Said XML copy, created on Dec. 7, 2022, is named P37294-US.xml and is 15,168 bytes in size.

The current invention is in the field of hydrolytic enzymes. More precisely, herein are reported methods for producing recombinant therapeutic polypeptide preparations with low levels of host-cell-related hydrolytic activity as well as methods for detecting such host-cell-related hydrolytic activity in polypeptide preparations and methods for the selection of host cells producing recombinant therapeutic polypeptides with low concomitant levels of host-cell-related hydrolytic activity.

BACKGROUND OF THE INVENTION

Polysorbates are used amongst other uses in biopharmaceutical protein formulations as stabilizers against protein aggregation and for preventing surface adsorption. Some studies show that residual hydrolytic activity/hydrolytically active host-cell proteins (HCPs) are present in the final biopharmaceutical formulations. Such hydrolytic activity/hydrolytically active HCPs are responsible for the hydrolysis of polysorbate during long-term storage. The hydrolysis of polysorbate within therapeutic protein formulations is leading to increased levels of free fatty acids. This is a major quality concern and represents a potential risk factor for product quality and shelf life. Since both the concentration and activity of hydrolytic HCPs in final formulations are in most cases extremely low, generally employed analytical methods are either insufficient in terms of sensitivity and/or do not offer a reasonable turn-around time for their detection.

Bhargava, A. C., et al. reported a high-throughput, fluorescence-based esterase activity assay for assessing polysorbate degradation risk during biopharmaceutical development (Pharm. Res. 38 (2021) 397-413).

Jahn, M., et al. reported the measuring of lipolytic activity to support process improvements to manage lipase-mediated polysorbate degradation (Pharm. Res. 37 (2020) 118).

WO 2021/050585 reported compositions, methods and kits for detection of lipolytic activity.

Glücklich, N., et al. reported the assessment of the polysorbate degradation fingerprints and kinetics of lipases and how the activity of polysorbate degrading hydrolases is influenced by the assay and assay conditions (Eur. J. Pharm. Sci. 166 (2021) 105980).

Li, X., et al. reported the profiling of active enzymes for polysorbate degradation in biotherapeutics by activity-based protein profiling (Anal. Chem. 93 (2021) 8161-8169).

WO 2001/73442 reported a biotin-PEG substrate for a lipase assay.

Li, X., et al. reported the measurement and control of high-risk host cell proteins for polysorbate degradation in biologics formulation (Antibod. Ther. 5 (2022) 42-54).

Zhang, S., et al. (Anal. Biochem. 637 (2022) 114472; available online 18 Nov. 2021) reported monitoring polysorbate hydrolysis in therapeutic proteins using an ultra-sensitive extraction-free fatty acid quantitation method.

Thus, there is the need for assays with improved properties.

SUMMARY OF THE INVENTION

Herein is reported a new assay setup using a tri-partite artificial substrate for a bond-cleaving enzyme that mimics a naturally occurring substrate of said bond-cleaving enzyme and allows the detection of the cleavage product with high sensitivity in short time to determine the bond-cleaving activity in a sample.

For example, in case a bond-cleaving enzyme is present in a sample to be analyzed, the artificial substrate will comprise exactly one bond that is susceptible of cleavage by said bond-cleaving enzyme of the class of enzymes to which the bond-cleaving enzyme in question is belonging. This cleavage-susceptible bond is cleaved by said enzyme, the intact artificial substrate as well as one of the cleavage products is removed, and the other cleavage product is subsequently detected. Therefore, the artificial substrate comprises three tags. One part of the substrate is conjugated to a first tag that allows removal of the intact artificial substrate and of one of the cleavage products from the sample after incubation. The second part of the substrate is conjugated to two tags, a first one for immobilization and a second one for detection. As first, second and third tag any tag useful according to the knowledge of the person skilled in the art can be used.

Thus, one aspect of the current invention is a method for determining bond-cleaving activity and/or the presence of a bond-cleaving enzyme in a sample, the method comprising the following steps:

a) mixing and incubating the sample or an aliquot thereof and a buffered solution to form an incubated sample,
  - wherein the buffered solution comprises a buffer substance, an artificial bond-cleaving enzyme substrate, a salt and optionally bovine serum albumin,
  - wherein the sample comprises a therapeutic polypeptide,
  - wherein the artificial bond-cleaving enzyme substrate comprises exactly one bond susceptible of being cleaved by the bond-cleaving enzyme to be detected, wherein said bond is covalently linking a first part of the substrate, which is conjugated to a first label, and a second part of the substrate, which is conjugated to a nucleic acid tag and a second label, which is different from the first label,
  - wherein the bond in the artificial bond-cleaving enzyme substrate is cleaved into a free first part and a free second part if the respective bond-cleaving activity and/or a respective bond-cleaving enzyme is present in the sample, b) removing the free first part and (not-cleaved=intact) artificial bond-cleaving enzyme substrate from the incubated sample to obtain a depleted sample,
  - wherein the removing is by contacting the incubated sample with a first solid phase, which specifically binds to the first label, (for a time sufficient so that the free first part and the (not-cleaved) artificial bond-cleaving enzyme substrate become bound to a ligand, which is conjugated to the solid phase and which specifically binds to the first label,) and separating the free first part- and (not-cleaved) artificial bond-cleaving enzyme substrate-depleted incubation mixture from the first solid phase thereafter, c) determining bond-cleaving activity and/or the presence of a bond-cleaving enzyme in the sample by determining the (amount of the) second label in the depleted sample, wherein the determining of bond-cleaving activity and/or the presence of a bond-cleaving enzyme in the sample is by capturing the second part on a second solid phase via the nucleic acid tag followed by detecting (by electrochemiluminescense) the solid-phase captured free second part with an antibody specifically binding to the second label, which antibody is conjugated to one or more detectable (ruthenium) labels, or wherein the determining of bond-cleaving activity and/or the presence of a bond-cleaving enzyme in the sample is by determining if the amount of the second label in the depleted sample exceeds the amount determined in a control sample free of/without bond-cleaving activity and/or the presence of a bond-cleaving enzyme.

Herein is reported especially a new assay setup using a tri-partite artificial hydrolase substrate that mimics a hydrolytically sensitive part of polysorbate and allows the detection of the hydrolytic cleavage product with high sensitivity in short time to determine hydrolase (hydrolytic) activity in a sample.

In case a hydrolase, such as, e.g. an esterase is present in sample to be analyzed, the artificial hydrolase substrate is cleaved by the hydrolase and the released alcohol part of the artificial substrate is subsequently detected.

In one preferred embodiment, the hydrolase is an esterase or a lipase. In one preferred embodiment, the detection is with an electrochemiluminescense immunoassay.

The current invention is based, at least in part, on the finding that with the method according to the invention the hydrolase (hydrolytic) activity in a sample can be determined within 48 hours or less, without the need of sample pre-treatment and without the need of chromatographic separation. Thus, the method of the current invention is improved as it allows the determination of hydrolase (hydrolytic) activity/the presence of hydrolases with improved speed compared to the FAMS assay, which requires 10 to 14 days (48 hours matches the frequency with which purification methods for biologicals can be performed to generate new samples), but with comparable sensitivity as well as with reduced handling requirements compared to other assays, as no sample pre-preparation, such as e.g. buffer exchange, or chromatography separation and equipment is required.

Further, the assay according to the current invention allows the determination of PS20 as well as PS80 degrading hydrolase (hydrolytic) activity/hydrolases with the same artificial enzyme substrate. Thereby the total or sum of hydrolase (hydrolytic) activity/hydrolases in a sample can be determined.

Further, the assay according to the current invention is high-throughput screening (HTS) suitable.

The invention is based, at least in part, on the finding that the use of an inert bovine serum albumin results in an increased signal-to-noise ratio and thereby an improved sensitivity. Without being bound by this theory, it is assumed that by using the inert bovine serum albumin the hydrolase (hydrolytic) enzymatic activity in the sample could be increased and thereby the sensitivity of the assay was increased. In one preferred embodiment, the inert bovine serum albumin is a bovine serum albumin with more than 80% of the cysteine residue at position 34 being oxidized/in oxidized form. In certain embodiments, more than 90% of the cysteine residue at position 34 is oxidized/in oxidized form. In certain embodiments, 95% or more of the cysteine residues at position 34 is oxidized/in oxidized form. In one preferred embodiment, more than 80% of the bovine serum albumin is present in monomeric form (not conjugated to a second polypeptide at cysteine residue 34). In certain embodiments, more than 90% of the bovine serum albumin is present in monomeric form. In certain embodiments, 95% or more of the bovine serum albumin is present in monomeric form.

The invention is based, at least in part, on the finding that the use of (3-(N-morpholino)propane sulfonic acid) (MOPS) as buffer in the method according to the invention results in a better assay sensitivity. Without being bound by this theory it is assume that the pKa value of MOPS of 7.02 at 37° C. is resulting in better buffering capacity at a pH value of 7.0.

The invention is based, at least in part, on the finding that the use of hybridizing LNA molecules as immobilization tag to capture the final analyte compared to a capture via, e.g., streptavidin/biotin results in an increased signal-to-noise ratio and thereby an improved sensitivity.

The invention is based, at least in part, on the finding that the sample does not require a pre-treatment in order to be suitable for the method according to the current invention, i.e. the method according to the current invention is independent of the sample matrix, such as, e.g., the buffer or pH of the sample.

The invention is based, at least in part, on the finding that the addition of about 0.1% (w/v) of a detergent, especially a non-ionic detergent, increases assay sensitivity. This is especially useful if purified samples, i.e. formulated drug substance, has to be tested, as thereby even minute amounts of residual hydrolase (hydrolytic) activity can be determined.

Thus, one aspect of the current invention is a method for determining hydrolase (hydrolytic) activity and/or the presence of a hydrolase in a sample, the method comprising the following steps:

a) mixing and incubating the sample or an aliquot thereof and a buffered solution to form an incubated sample, wherein the buffered solution comprises a buffer substance, an artificial hydrolase substrate, a salt and bovine serum albumin, wherein the sample comprises a therapeutic polypeptide, wherein the artificial hydrolase substrate comprises a single/exactly one ester bond covalently linking a carboxylic acid residue, which is conjugated to a first label, and an alcohol residue, which is conjugated to a nucleic acid tag and a second label, which is different from the first label, wherein the ester bond in the artificial hydrolase substrate is cleaved into a free alcohol residue and a free carboxylic acid residue if hydrolase (hydrolytic) activity and/or a hydrolase is present in the sample, b) removing the free carboxylic acid residue and (not-cleaved) artificial hydrolase substrate from the incubated sample to obtain a depleted sample, wherein the removing is by contacting the incubated sample with a first solid phase, which specifically binds to the first label, (for a time sufficient so that the free carboxylic acid and the (not-cleaved) artificial hydrolase substrate become bound to a ligand, which is conjugated to the solid phase and which specifically binds to the first label,) and separating the free carboxylic acid- and (not-cleaved) artificial hydrolase substrate-depleted incubation mixture from the first solid phase thereafter, c) determining hydrolase (hydrolytic) activity and/or the presence of a hydrolase in the sample by determining the (amount of the) second label in the depleted sample,
   wherein the determining of hydrolase (hydrolytic) activity and/or the presence of a hydrolase in the sample is by capturing the free alcohol residue on a second solid phase via the nucleic acid tag followed by detecting (by electrochemiluminescense) the solid-phase captured free alcohol residue with an antibody specifically binding to the second label, which antibody is conjugated to one or more detectable (ruthenium) labels,
   or
   wherein the determining of hydrolase (hydrolytic) activity and/or the presence of a hydrolase in the sample is by determining if the amount of the second label in the depleted sample exceeds the amount determined in a control sample free of/without hydrolase activity and/or the presence of a hydrolase.

One aspect of the current invention is a method for determining hydrolase activity in a sample, the method comprising the following steps:

a) mixing and incubating an aliquot of the sample and a buffered solution for a defined period of time to form an incubated sample,
   wherein the buffered solution comprises a buffer substance, an artificial hydrolase substrate, a salt and bovine serum albumin,
   wherein the sample comprises a therapeutic polypeptide,
   wherein the artificial hydrolase substrate comprises a single/exactly one ester bond covalently linking a carboxylic acid residue, which is conjugated to a first label, and an alcohol residue, which is conjugated to a nucleic acid tag and a second label, which is different from the first label,
   wherein the ester bond in the artificial hydrolase substrate is cleaved into a free alcohol residue and a free carboxylic acid residue if hydrolase (hydrolytic) activity and/or a hydrolase is present in the sample,
b) removing the free carboxylic acid residue and (not-cleaved) artificial hydrolase substrate from the incubated sample to obtain a depleted sample,
   wherein the removing is by contacting the incubated sample with a first solid phase, which specifically binds to the first label, (for a time sufficient so that the free carboxylic acid and the (not-cleaved) artificial hydrolase substrate become bound to a ligand, which is conjugated to the solid phase and which specifically binds to the first label,) and separating the free carboxylic acid- and (not-cleaved) artificial hydrolase substrate-depleted incubation mixture from the first solid phase thereafter,
c) optionally repeating steps a) to b) at least once with a further (new) aliquot of the sample for a period of time different from all previous periods used in step a),
d) determining the (amount of the) second label in (each of) the depleted sample(s) (individually),
   wherein the determining is by capturing the free alcohol residue on a second solid phase via the nucleic acid tag followed by detecting (by electrochemiluminescense) the captured free alcohol residue with an antibody specifically binding to the second label, which antibody is conjugated to one or more detectable (ruthenium) labels,
e) determining the hydrolase activity or hydrolase activity kinetics over time in the sample by quantifying the amount of second label present in the depleted sample, optionally individually for all periods of time, using a calibration curve.

One aspect of the current invention is a method for selecting a (recombinant) mammalian cell clone, the method comprising the following steps:

1) separately determining for cultivation supernatant samples obtained by separately cultivating at least two different (recombinant) mammalian cell clones the hydrolase activity by
   a) mixing and incubating the cultivation supernatant sample or an aliquot thereof and a buffered solution to form an incubated mixture,
      wherein the buffered solution comprises a buffer substance, an artificial hydrolase substrate, a salt and bovine serum albumin,
      wherein the sample comprises a therapeutic polypeptide,
      wherein the artificial hydrolase substrate comprises a single/exactly one ester bond covalently linking a carboxylic acid residue, which is conjugated to a first label, and an alcohol residue, which is conjugated to a nucleic acid tag and a second label, which is different from the first label,
      wherein the ester bond in the artificial hydrolase substrate is cleaved into a free alcohol residue and a free carboxylic acid residue if hydrolase (hydrolytic) activity and/or a hydrolase is present in the sample,
   b) removing the free carboxylic acid residue and (not-cleaved) artificial hydrolase substrate from the incubated mixture to obtain a depleted mixture,
      wherein the removing is by contacting the incubated mixture with a first solid phase, which specifically binds to the first label, (for a time sufficient so that the free carboxylic acid residue and the (not-cleaved) artificial hydrolase substrate become bound to a ligand, which is conjugated to the solid phase and which specifically binds to the first label,) and separating the free carboxylic acid- and (not-cleaved) artificial hydrolase substrate-depleted incubation mixture from the first solid phase thereafter,
   c) determining hydrolase (hydrolytic) activity in the sample by determining the (amount of the) second label in the depleted sample,
      wherein the determining is by capturing the free alcohol residue on a second solid phase via the nucleic acid tag followed by detecting (by electrochemiluminescense) the captured free alcohol residue with an antibody specifically binding to the second label, which antibody is conjugated to one or more detectable (ruthenium) labels,
2) selecting the mammalian cell clone with the lowest hydrolase (hydrolytic) activity determined in step c).

In one preferred embodiment of all aspects and other embodiments of the invention, the hydrolase is an esterase and the hydrolase activity is esterase activity.

In one preferred embodiment of all aspects and other embodiments of the invention, the detection is with an electrochemiluminescense immunoassay.

In certain embodiments of all aspects and other embodiments of the invention, the first and the second label is selected independently of each other from the group consisting of antigens and partners of specific binding pairs.

In certain embodiments of all aspects and other embodiments of the invention, the nucleic acid tag can stably hybridize with a second complementary nucleic acid molecule. In certain embodiments, the nucleic acid tag is a locked nucleic acid/LNA oligonucleotide. In one preferred embodiment, all nucleotides of the nucleic acid tag are locked nucleic acid monomers. In certain embodiments of all aspects and other embodiments of the invention, the nucleic acid sequence tag is selected from the group consisting of

```
SEQ ID NO: 01: tgctcctg;

SEQ ID NO: 02: caggagca;

SEQ ID NO: 09: tgctcctgt;

SEQ ID NO: 10: acaggagca;

SEQ ID NO: 11: gtgcgtct;

SEQ ID NO: 12: agacgcac;

SEQ ID NO: 13: gttggtgt;

SEQ ID NO: 14: acaccaac;

SEQ ID NO: 33: cttcc;

SEQ ID NO: 34: ggaag;

SEQ ID NO: 42: gctcc;

SEQ ID NO: 43: ggagc;

SEQ ID NO: 16: gttggt;

SEQ ID NO: 46: ccaac;

SEQ ID NO: 16: gttggt;

SEQ ID NO: 19: caccaac;

SEQ ID NO: 16: gttggt;

SEQ ID NO: 17: caacacaccaac;

SEQ ID NO: 16: gttggt;

SEQ ID NO: 18: acacaccaac;

SEQ ID NO: 16: gttggt;

SEQ ID NO: 14: acaccaac;

SEQ ID NO: 16: gttggt;

SEQ ID NO: 20: accaac;

SEQ ID NO: 40: ctgtca;

SEQ ID NO: 41: tgacag;

SEQ ID NO: 44: tgctcc;

SEQ ID NO: 45: ggagca;

SEQ ID NO: 35: tettcc;
```

-continued

```
SEQ ID NO: 36: ggaaga;

SEQ ID NO: 21: gttggtg;

SEQ ID NO: 17: caacacaccaac;

SEQ ID NO: 21: gttggtg;

SEQ ID NO: 18: acacaccaac;

SEQ ID NO: 21: gttggtg;

SEQ ID NO: 14: acaccaac;

SEQ ID NO: 21: gttggtg;

SEQ ID NO: 19: caccaac;

SEQ ID NO: 21: gttggtg;

SEQ ID NO: 20: accaac;

SEQ ID NO: 01: tgctcctg;

SEQ ID NO: 02: caggagca;

SEQ ID NO: 11: gtgcgtct;

SEQ ID NO: 12: agacgcac;

SEQ ID NO: 13: gttggtgt;

SEQ ID NO: 17: caacacaccaac;

SEQ ID NO: 13: gttggtgt;

SEQ ID NO: 18: acacaccaac;

SEQ ID NO: 13: gttggtgt;

SEQ ID NO: 14: acaccaac;

SEQ ID NO: 13: gttggtgt;

SEQ ID NO: 19: caccaac;

SEQ ID NO: 13: gttggtgt;

SEQ ID NO: 20: accaac;

SEQ ID NO: 22: gttggtgtg;

SEQ ID NO: 17: caacacaccaac;

SEQ ID NO: 22: gttggtgtg;

SEQ ID NO: 18: acacaccaac;

SEQ ID NO: 22: gttggtgtg;

SEQ ID NO: 14: acaccaac;

SEQ ID NO: 22: gttggtgtg;

SEQ ID NO: 19: caccaac;

SEQ ID NO: 22: gttggtgtg;

SEQ ID NO: 20: accaac;

SEQ ID NO: 09: tgctcctgt;

SEQ ID NO: 15: caggagc;

SEQ ID NO: 09: tgctcctgt;

SEQ ID NO: 10: acaggagca;

SEQ ID NO: 09: tgctcctgt;

SEQ ID NO: 02: caggagca;
```

-continued

```
SEQ ID NO: 22: gttggtgtg;

SEQ ID NO: 30: cacaccaac;

SEQ ID NO: 37: ttctcttcc;

SEQ ID NO: 38: ggaagagaa;

SEQ ID NO: 23: gttggtgtgttg;

SEQ ID NO: 17: caacacaccaac;

SEQ ID NO: 23: gttggtgtgttg;

SEQ ID NO: 18: acacaccaac;

SEQ ID NO: 23: gttggtgtgttg;

SEQ ID NO: 14: acaccaac;

SEQ ID NO: 23: gttggtgtgttg;

SEQ ID NO: 19: caccaac;

SEQ ID NO: 23: gttggtgtgttg:

SEQ ID NO: 20: accaac;

SEQ ID NO: 31: gttggtgtgttggtg;

SEQ ID NO: 32: caccaacacaccaac;

SEQ ID NO: 28: aaaaaaaaa;

SEQ ID NO: 24: ttttttttt;

SEQ ID NO: 28: aaaaaaaaa;

SEQ ID NO: 25: tttttttt;

SEQ ID NO: 28: aaaaaaaaa;

SEQ ID NO: 26: tttttt;

SEQ ID NO: 28: aaaaaaaaa;

SEQ ID NO: 27: tttttt;

SEQ ID NO: 39: aaaaaa;

SEQ ID NO: 27: tttttt;
```

In one preferred embodiment, the nucleic acid tag has the sequence in 3'- to 5'-direction TGGTTG. In certain embodiments, the nucleic acid tag specifically and stably hybridizes with the nucleic acid sequence CAACCA (in 3'- to 5'-direction). In one preferred embodiment, the pair of two separate compatible binding partners is the pair of all-LNA single-stranded-oligonucleotides of SEQ ID NO: 16 and SEQ ID NO: 20.

In certain embodiments of all aspects and other embodiments of the invention, the buffered solution further comprises sodium chloride.

In certain embodiments of all aspects and other embodiments of the invention, the alcohol of the artificial hydrolase substrate and the carboxylic acid of the artificial hydrolase substrate each comprises independently of each other one or more ethylene oxide ($CH_2$—$CH_2$—O) units.

In certain embodiments of all aspects and other embodiments of the invention, the artificial hydrolase substrate comprises wherein n and m each and independently of each other zero or a positive integer value, R1 comprises the first label, and R2, R3 comprises the second label and the nucleic acid tag.

One independent aspect of the invention is the artificial hydrolase substrate. This is a means for performing the assay according to the invention.

In certain embodiments of all aspects and other embodiments of the invention, the buffered solution has a pH value of about 7.

In certain embodiments of all aspects and other embodiments of the invention, the incubating is at a temperature in the range of 25° C. to 45° C. In certain embodiments, the incubating is at a temperature in the range of 33° C. to 41° C.

In certain embodiments, the incubating is at a temperature in the range of 37° C. to 40° C. In certain embodiment, the incubating is at a temperature of about 37° C.

In certain embodiments of all aspects and other embodiments of the invention, the incubating is for at least 15 minutes and up to 36 hours. In certain embodiments, up to 22 hours. In certain embodiments, up to 8 hours.

In certain embodiments of all aspects and other embodiments of the invention, the incubation mixture comprises a final concentration of 300 μM or less bovine serum albumin. In certain embodiments, the incubation mixture comprises a final concentration of 30 μM or less bovine serum albumin. In one preferred embodiment, the incubation mixture comprises a final concentration of 10 μM or less bovine serum albumin. In one preferred embodiment, the incubation mixture comprises about 6 μM bovine serum albumin.

In certain embodiments of all aspects and other embodiments of the invention, the incubation mixture comprises a divalent metal ion. In one preferred embodiment, the divalent metal ion is $Mg^{2+}$. In certain embodiments, the divalent metal ion is added in form of a chloride salt. In certain embodiments, the divalent metal ion is (added as) $MgCl_2$.

In certain embodiments of all aspects and other embodiments of the invention, the incubation mixture further comprises a detergent at a final concentration of 0.05% to 0.15% (w/v). In one preferred embodiment, the final concentration of the detergent is about 0.1% (w/v). In certain embodiments, the detergent is a non-ionic detergent.

In certain embodiments of all aspects and other embodiments of the current invention, the detergent is Triton X-100. In certain embodiments, the detergent is an aromatic hydrocarbon lipophilic or hydrophobic group with hydrophilic polyethylene oxide chains. In certain embodiments, the detergent has on average it has 9.5 ethylene oxide units and the hydrocarbon is a 4-(1,1,3,3-tetramethylbutyl)-phenyl group.

In certain embodiments of all aspects and other embodiments of the current invention, the detergent is Triton CG-110. In other certain embodiments, the detergent is an alkyl polyglucoside. In one preferred embodiment, the detergent is a mixture of 58.0-62.0 (w/v) % D-glucopyranose, oligomeric, decyl octyl glycoside and 38.0-42.0 (w/v) % water.

In certain embodiments of all aspects and other embodiments of the current invention, the incubation mixture comprises 20-30 mM sodium chloride, 3-10 μM BSA with a monomeric content of 95% or more/with oxidized Cys34, 100-200 mM MOPS, 3-10 mM magnesium chloride, 0.05-0.15% (w/v) detergent, the therapeutic polypeptide has a concentration of 0.1-250 mg/mL, has at pH value of 6.8 to 7.2, and the incubation is performed at 35-40° C. for 8 to 36 hours.

In one preferred embodiment of all aspects and other embodiments of the invention, the incubation mixture comprises a final concentration of about 300 mM TRIS, about 5 mM $MgCl_2$, about 25 mM NaCl, about 0.1% (w/v) triton CG-110, and about 6 μM bovine serum albumin.

In one preferred embodiment of all aspects and other embodiments of the invention, the buffered solution comprises about 150 mM MOPS, about 5 mM $MgCl_2$, about 25 mM NaCl, about 0.1% (w/v) triton CG-110, and about 6 μM bovine serum albumin.

In one preferred embodiment of all aspects and other embodiments of the invention, the first label is biotin or a variant thereof or the first label is (strept)avidin or a variant thereof.

In one preferred embodiment of all aspects and other embodiments of the invention, the second label is digoxygenin or a variant thereof.

In certain embodiments of all aspects and other embodiments of the invention, the mammalian cell clone is a recombinant mammalian cell clone comprising one or more nucleic acids encoding a therapeutic polypeptide. In certain embodiments, the therapeutic polypeptide is a heterologous therapeutic polypeptide. In certain embodiments, the therapeutic polypeptide is an antibody. In one preferred embodiment, the (recombinant) mammalian cell clone is a stable transfected CHO cell clone expressing an antibody, preferably a bispecific antibody. In certain embodiments, the cell clone produces/the cell clones produce a multispecific antibody. In certain embodiments, one of the binding specificities of the multispecific antibody is for a first antigen and the other is for a different second antigen. In certain embodiments, the multispecific antibody binds to two different epitopes of the same antigen. In certain embodiments, the second epitope on the same antigen is a non-overlapping epitope. In certain embodiments, the antibody is a bispecific antibody. In certain embodiments, the bispecific antibody is a trivalent, bispecific antibody or a bivalent, bispecific antibody. In certain embodiments, the multispecific antibody comprises a Fab fragment, in which either the variable regions or the constant regions of the heavy and light chain are exchanged, i.e. wherein in one chain a heavy chain VH variable domain is either directly of via a peptidic linker conjugated to a light chain CL constant domain, and in the respective other chain a light chain VL variable domain is either directly of via a peptidic linker conjugated to a heavy chain CH1 constant domain.

In certain embodiments of all aspects and other embodiments of the invention, the ester bond between the alcohol residue and the carboxylic acid residue in the artificial hydrolase substrate is susceptible to cleavage by a hydrolase.

In certain embodiments of all aspects and other embodiments of the invention, the incubating is to have the ester bond in the artificial hydrolase substrate cleaved by the hydrolase/hydrolase activity in the sample.

In certain embodiments of all aspects and other embodiments of the invention, the hydrolase/hydrolase activity is based on the presence of one or more hydrolase(s) selected from the group consisting of Lipoprotein Lipase, Palmitoyl Proteinthioesterase, Acid Ceramidase, the C-terminal domain of Fatty Acid synthase, Putative Phospholipase b-like 2, Lysosomal Acid Lipase, Lysosomal Phospholipase, and Sialate O-Acetylesterase.

In certain embodiments of all aspects and other embodiments of the invention, the hydrolase/hydrolase activity is based on the presence of one or more hydrolase(s) selected from the group consisting of Lipoprotein Lipase, Palmitoyl Proteinthioesterase, Acid Ceramidase, the C-terminal domain of Fatty Acid synthase, Putative Phospholipase b-like 2, Lysosomal Acid Lipase, Lysosomal Phospholipase, and Sialate O-Acetylesterase.

In certain embodiments of all aspects and other embodiments of the invention, the incubated mixture comprises non-cleaved artificial hydrolase substrate and the cleavage products of the artificial hydrolase substrate. In certain embodiments, the cleavage products of the artificial hydrolase substrate are the free alcohol residue and the free carboxylic acid residue.

In certain embodiments of all aspects and other embodiments of the invention, the depleted incubation mixture is depleted of the free carboxylic acid residue and non-cleaved artificial hydrolase substrate.

In certain embodiments of all aspects and other embodiments of the invention, the hydrolase is a lipase.

In certain embodiments of all aspects and other embodiments of the current invention, the hydrolase is selected from the group consisting of Lipoprotein Lipase (Accession number: G3H6V7), Palmitoyl Proteinthioesterase 1 (Accession number: G3HN89), Acid Ceramidase (Accession number: G3GZB2), the C-terminal domain of Fatty Acid synthase (Accession number: G3GXD7), Putative Phospholipase b-like 2 (Accession number: G316T1), Lysosomal Acid Lipase (Accession number: G3HQY6), Lysosomal Phospholipase, Phospholipase A2, group VII (PLA2G7) and group XV (PLA2G15), Sialate O-Acetylesterase. In certain embodiments, the hydrolase is Lipoprotein Lipase, Putative Phospholipase b-like 2, and/or Lysosomal Phospholipase. In one preferred embodiment, the hydrolase is Lysosomal Phospholipase, specifically lysosomal phospholipase A2 (LPLA2) (Accession number: G3HKV9).

In certain embodiments of all aspects and other embodiments of the invention, the sample is not pre-treated. In certain embodiments, the sample is used without buffer exchange. In certain embodiments, the sample is used without chromatographic pre-separation. In one preferred embodiment, the sample is a crude cultivation supernatant or a crude preparative chromatography column eluate.

In certain embodiments of all aspects and other embodiments of the invention, the method is for determining the total hydrolytic/hydrolase activity in a sample.

In addition to the various aspects and embodiments depicted and claimed, the disclosed subject matter is also directed to other aspects and embodiments having other combinations of the features disclosed and claimed herein. As such, the particular features presented herein, especially presented as aspects or embodiments, can be combined with each other in other manners within the scope of the disclosed subject matter such that the disclosed subject matter includes any suitable combination of the features disclosed herein. The description of specific embodiments of the disclosed subject matter has been presented for purposes of illustration and description. It is not intended to be exhaustive or to limit the disclosed subject matter to those embodiments disclosed.

DETAILED DESCRIPTION OF THE INVENTION

Herein is reported a new assay setup using a tri-partite artificial hydrolase substrate that mimics polysorbate. If a hydrolase or a compound with hydrolase activity is present in a sample to be analyzed, the artificial hydrolase substrate is cleaved by the hydrolase/hydrolase activity and the released alcohol residue of the artificial hydrolase substrate is detected. The detection of the released alcohol residue of the artificial hydrolase substrate is by a label attached thereto. The label can be freely chosen. Therefore, the detection can be by any known method, such as, e.g., Simoa®, Gyrolab®, Elecsys®, ELISA, etc. In one preferred embodiment, the detection is with an electrochemiluminescense immunoassay.

The invention is based, at least in part, on the finding that the presence of bovine serum albumin with high monomeric content is advantageous with respect to assay sensitivity. Thereby the hydrolytic enzymatic activity of hydrolases (hydrolase activity) as well as the sensitivity of the assay could be increased.

General

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation of derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In certain embodiments, the term about denotes a range of +/−10% of the thereafter following numerical value. In certain embodiments, the term about denotes a range of +/−5% of the thereafter following numerical value.

The term "comprising" also encompasses the term "consisting of".

Cells

The term "cell clone" as used herein denotes a mammalian cell comprising an exogenous nucleotide sequence capable of expressing a polypeptide, i.e. is a recombinant mammalian cell. Such recombinant mammalian cells are cells into which one or more exogenous nucleic acid(s) have been introduced, including the progeny of such cells. In certain embodiments, the cell clone is a mammalian cell comprising a nucleic acid encoding a heterologous polypeptide. Thus, the term "cell clone comprising a nucleic acid encoding a heterologous polypeptide" denotes recombinant mammalian cells comprising an exogenous nucleotide sequence integrated in the genome of the mammalian cell and capable of expressing the heterologous polypeptide. In certain embodiments, the cell clone is a mammalian cell comprising an exogenous nucleotide sequence integrated at a single site within a locus of the genome of the cell. In one preferred embodiment, the cell clone is a mammalian cell comprising an exogenous nucleotide sequence integrated at a single site within a locus of the genome of the cell, wherein the exogenous nucleotide sequence comprises a first and a second recombination recognition sequence flanking at least one first selection marker, and a third recombination recognition sequence located between the first and the second recombination recognition sequence, and all the recombination recognition sequences are different.

The term "recombinant cell" as used herein denotes a cell after genetic modification, such as, e.g., a cell expressing a heterologous polypeptide of interest and that can be used for the production of said heterologous polypeptide of interest at any scale. For example, "a cell clone" denotes a cell wherein the coding sequences for a heterologous polypeptide of interest have been stably introduced into the genome. For example, "a recombinant mammalian cell comprising an exogenous nucleotide sequence" that has been subjected to recombinase mediated cassette exchange (RMCE), whereby the coding sequences for a polypeptide of interest have been stably introduced into the genome of the host cell, is a specific "cell clone".

A "cell clone" as used herein includes the primary transformed cell as well as progeny derived therefrom without regard to the number of passages. Progeny may, e.g., not be completely identical in nucleic acid content to a parent cell, but may contain mutations. Mutant progeny that has the same function or biological activity as screened or selected for in the originally transformed cell are encompassed.

An "isolated cell clone" denotes a cell clone, which has been separated from a component of its natural environment.

An "isolated nucleic acid" denotes a nucleic acid molecule that has been separated from a component of its natural environment.

An "isolated polypeptide" or an "isolated antibody" or an "isolated side product" denotes a polypeptide molecule or an antibody molecule, respectively, that has been separated from a component of its natural environment. In certain embodiments, an isolated polypeptide or an isolated antibody is purified to greater than 95% or 99% purity as determined by, for example, electrophoretic (e.g., SDS-PAGE, isoelectric focusing (IEF), capillary electrophoresis, CE-SDS) or chromatographic (e.g., size exclusion chromatography or ion exchange or reverse phase HPLC). For review of methods for assessment of e.g. antibody purity, see, e.g., Flatman, S. et al., J. Chrom. B 848 (2007) 79-87.

Assays

The detection of the released alcohol residue of the artificial hydrolase substrate in the method according to the invention is by a label attached thereto. The label can be freely chosen. Therefore, the detection can be by any known method, such as, e.g., Simoa®, Gyrolab®, Elecsys®, ELISA, etc.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

The term "immunoassay" denotes any technique that utilizes specifically binding molecules, such as antibodies, to capture and/or detect a specific target for qualitative or quantitative analysis. In general, an immunoassay is characterized by the following steps: 1) immobilization or capture of the analyte and 2) detection and measuring the analyte. The analyte can be captured, i.e. bound, on any solid surface, such as e.g. a membrane, plastic plate, or some other solid surface.

Generally, immunoassays can be performed in three different formats. One is with direct detection, one with indirect detection, or by a sandwich assay.

The direct detection immunoassay uses a detection (or tracer) antibody that can be measured directly. An enzyme or other molecule or radiation allows for the generation of a signal that will produce a color, fluorescence, or electrochemiluminescense that allow the signal to be visualized or measured.

In an indirect assay, a primary antibody that binds to the analyte is used to provide a defined target for a secondary antibody that specifically binds to the target provided by the primary antibody (referred to as detector or tracer antibody). The secondary antibody generates the measurable signal.

The sandwich assay makes use of two reagents, a capture and a tracer (detector) reagent. The capture reagent is used to bind (immobilize) the analyte from the solution. This allows the analyte to be specifically removed from the sample. The tracer (detector) reagent is used in a second step to generate a signal (either directly or indirectly as described above). The sandwich format requires two reagents each with a distinct binding site on the analyte. In addition, they must not interfere with one another, as both reagents must be bound to the target at the same time.

Amino acids comprise different reactive side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of amino acid side chains is the aliphatic ε-amine of the amino acid lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with proteinaceous amines in aqueous solution (optimally at pH 9.0 to 9.5). Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with terminal and F-amine groups of amino acids to form amide linkages. The anhydride rings open to create multivalent, metal-chelating arms able to bind tightly to metals in a coordination complex.

Another common reactive group is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiotreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido] hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group are carboxylic acids. Polypeptides contain carboxylic acid groups at the C-terminal position and within the side chains of aspartic acid and glutamic acid. The relatively low reactivity of carboxylic acids in water usually makes it difficult to use these groups to selectively modify polypeptides. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety to an aldehyde. Each aldehyde group can be reacted with an amine, hydrazide, or hydrazine as described for carboxylic acids. A Schiff's base intermediate is formed, which can be reduced to an alkyl amine through the reduction of the intermediate with sodium cyanoborohydride (mild and selective) or sodium borohydride (strong) water-soluble reducing agents.

The conjugation of a polypeptide or amino acid to its conjugation partner can be performed by different methods, such as chemical binding, or binding via a binding pair. The term "conjugation partner" as used herein denotes e.g. solid supports, polypeptides, detectable labels, members of specific binding pairs. In certain embodiments, the conjugation of the polypeptide or amino acid to its conjugation partner is performed by chemically binding via N-terminal and/or ε-amino groups (lysine), ε-amino groups of different lysins, carboxy-, sulfhydryl-, hydroxyl-, and/or phenolic functional groups of the amino acid backbone of the antibody, and/or sugar alcohol groups of the carbohydrate structure. In one preferred embodiment, the carboxylic acid residue is conjugated to biotin and immobilization to a solid support is performed via solid support immobilized avidin or streptavidin. In one preferred embodiment, the alcohol residue is conjugated to digoxygenin by a covalent bond.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of substances may be used. Such particles include polymer particles such as polystyrene and poly (methyl methacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

Chromogens (fluorescent or luminescent groups and dyes), enzymes, NMR-active groups or metal particles are examples of "detectable labels". Metal chelates, which can be detected by electrochemiluminescense, are also signal-emitting groups, with particular preference being given to ruthenium chelates, e.g. a ruthenium $(bispyridyl)_3^{2+}$ chelate. Suitable ruthenium labeling groups are described, for example, in EP 0 580 979, WO 90/05301, WO 90/11511, and WO 92/14138. For direct detection, the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Examples of binding pairs are antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. In one preferred embodiment, the first binding pair members comprise hapten, antigen and hormone. In certain embodiments, the hapten is selected from the group consisting of digoxin, digoxygenin and biotin and analogues thereof. The second partner of such binding pair, e.g. an antibody, Streptavidin, etc., usually is labeled to allow for direct detection, e.g., by the labels as mentioned above.

Antibodies

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

The term "antibody" herein is used in the broadest sense and encompasses various antibody structures, including but not limited to full length antibodies, monoclonal antibodies, multispecific antibodies (e.g., bispecific antibodies), and antibody-antibody fragment-fusions as well as combinations thereof.

The term "full length antibody" denotes an antibody having a structure substantially similar to that of a native antibody. A full length antibody comprises two full length antibody light chains each comprising in N- to C-terminal direction a light chain variable region and a light chain constant domain, as well as two full length antibody heavy chains each comprising in N- to C-terminal direction a heavy chain variable region, a first heavy chain constant domain, a hinge region, a second heavy chain constant domain and a third heavy chain constant domain. In contrast to a native antibody, a full length antibody may comprise further immunoglobulin domains, such as e.g. one or more additional scFvs, or heavy or light chain Fab fragments, or scFabs conjugated to one or more of the termini of the different chains of the full length antibody, but only a single fragment to each terminus. These conjugates are also encompassed by the term full-length antibody.

The term "antibody binding site" denotes a pair of a heavy chain variable domain and a light chain variable domain. To ensure proper binding to the antigen these variable domains are cognate variable domains, i.e. belong together. An antibody the binding site comprises at least three HVRs (e.g. in case of a VHH) or three-six HVRs (e.g. in case of a naturally occurring, i.e. conventional, antibody with a VH/VL pair). Generally, the amino acid residues of an antibody that are responsible for antigen binding are forming the binding site. These residues are normally contained in a pair of an antibody heavy chain variable domain and a corresponding antibody light chain variable domain. The antigen-binding site of an antibody comprises amino acid residues from the "hypervariable regions" or "HVRs". "Framework" or "FR" regions are those variable domain regions other than the hypervariable region residues as herein defined. Therefore, the light and heavy chain variable domains of an antibody comprise from N- to C-terminus the regions FR1, HVR1, FR2, HVR2, FR3, HVR3 and FR4. Especially, the HVR3 region of the heavy chain variable domain is the region, which contributes most to antigen binding and defines the binding specificity of an antibody. A "functional binding site" is capable of binding to its target. The term "binding to" denotes the binding of a binding site to its target in an in vitro assay, in certain embodiments, in a binding assay. Such binding assay can be any assay as long the binding event can be detected. "Binding" can be determined using, for example, an ELISA assay.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the heavy chain variable domain VH (H1, H2, H3), and three in the light chain variable domain VL (L1, L2, L3).

HVRs Include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The "class" of an antibody refers to the type of constant domains or constant region, preferably the Fc-region, possessed by its heavy chains. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "heavy chain constant region" denotes the region of an immunoglobulin heavy chain that contains the constant domains, i.e. the CH1 domain, the hinge region, the CH2 domain and the CH3 domain. In one embodiment, a human IgG constant region extends from Ala118 to the carboxyl-terminus of the heavy chain (numbering according to Kabat EU index). However, the C-terminal lysine (Lys447) of the constant region may or may not be present (numbering according to Kabat EU index). The term "constant region" denotes a dimer comprising two heavy chain constant regions, which can be covalently linked to each other via the hinge region cysteine residues forming inter-chain disulfide bonds.

The term "heavy chain Fc-region" denotes the C-terminal region of an immunoglobulin heavy chain that contains at least a part of the hinge region (middle and lower hinge region), the CH2 domain and the CH3 domain. In one embodiment, a human IgG heavy chain Fc-region extends from Asp221, or from Cys226, or from Pro230, to the carboxyl-terminus of the heavy chain (numbering according to Kabat EU index). Thus, an Fc-region is smaller than a constant region but in the C-terminal part identical thereto. However, the C-terminal lysine (Lys447) of the heavy chain Fc-region may or may not be present (numbering according to Kabat EU index). The term "Fc-region" denotes a dimer comprising two heavy chain Fc-regions, which can be covalently linked to each other via the hinge region cysteine residues forming inter-chain disulfide bonds.

The term "valent" as used within the current application denotes the presence of a specified number of binding sites in an antibody. As such, the terms "bivalent", "tetravalent", and "hexavalent" denote the presence of two binding site, four binding sites, and six binding sites, respectively, in an antibody.

A "monospecific antibody" denotes an antibody that has a single binding specificity, i.e. specifically binds to one antigen. Monospecific antibodies can be prepared as full-length antibodies or antibody fragments (e.g. $F(ab')_2$) or combinations thereof (e.g. full length antibody plus additional scFv or Fab fragments). A monospecific antibody does not need to be monovalent, i.e. a monospecific antibody may comprise more than one binding site specifically binding to the one antigen. A native antibody, for example, is monospecific but bivalent.

A "multispecific antibody" denotes an antibody that has binding specificities for at least two different epitopes on the same antigen or two different antigens. Multispecific antibodies can be prepared as full-length antibodies or antibody fragments (e.g. Fab bispecific antibodies) or combinations thereof (antibody-antibody fragment-fusions, e.g. a full-length antibody conjugated to an additional scFv or Fab fragments). A multispecific antibody is at least bivalent, i.e. comprises two antigen binding sites. In addition, a multispecific antibody is at least bispecific. Thus, a bivalent, bispecific antibody is the simplest form of a multispecific antibody. Engineered antibodies with two, three or more (e.g. four) functional antigen binding sites have also been reported (see, e.g., US 2002/0004587).

In certain embodiments of all aspects and other embodiments of the invention, the cell clone produces/the cell clones produce a multispecific antibody. In certain embodiments, one of the binding specificities is for a first antigen and the other is for a different second antigen. In certain embodiments, the multispecific antibody binds to two different epitopes of the same antigen. In certain embodiments, the second epitope on the same antigen is a non-overlapping epitope. In certain embodiments, the antibody is a bispecific antibody. In one preferred embodiment, the bispecific antibody is a trivalent, bispecific antibody or a bivalent, bispecific antibody.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553); using the common light chain technology for circumventing the light chain mis-pairing problem (see, e.g., WO 98/50431); using specific technology for making bispecific antibody fragments (see, e.g., Holliger, P., et al., Proc. Natl. Acad. Sci. USA 90 (1993) 6444-6448); and preparing trispecific antibodies as described, e.g., in Tutt, A., et al., J. Immunol. 147 (1991) 60-69).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The bispecific antibody or antigen binding fragment thereof also includes a "Dual Acting Fab" or "DAF" (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see, e.g., WO 2009/080252 and WO 2015/150447), the CH1/CL domains (see, e.g., WO 2009/080253) or the complete Fab arms (see e.g., WO 2009/080251, WO 2016/016299, also see Schaefer et al., Proc. Natl. Acad. Sci. USA 108 (2011) 1187-1191, and Klein at al., MAbs 8 (2016) 1010-1020).

In one preferred embodiment of all aspects and other embodiments of the invention, the multispecific antibody comprises a Fab fragment, in which either the variable regions or the constant regions of the heavy and light chain are exchanged, i.e. wherein in one chain a heavy chain VH variable domain is either directly of via a peptidic linker conjugated to a light chain CL constant domain, and in the respective other chain a light chain VL variable domain is either directly of via a peptidic linker conjugated to a heavy chain CH1 constant domain.

Thus, a domain exchanged Fab fragment comprises a polypeptide chain composed of the light chain variable region (VL) and the heavy chain constant region 1 (CH1), and a polypeptide chain composed of the heavy chain variable region (VH) and the light chain constant region (CL).

Asymmetrical Fab arms can also be engineered by introducing charged or non-charged amino acid mutations into domain interfaces to direct correct Fab pairing. See e.g., WO 2016/172485.

The antibody or fragment can also be a multispecific antibody as described in WO 2009/080254, WO 2010/112193, WO 2010/115589, WO 2010/136172, WO 2010/145792, or WO 2010/145793.

The antibody or fragment thereof may also be a multispecific antibody as disclosed in WO 2012/163520.

Various further molecular formats for multispecific antibodies are known in the art and are included herein (see e.g., Spiess et al., Mol. Immunol. 67 (2015) 95-106).

Bispecific antibodies are generally antibody molecules that specifically bind to two different, non-overlapping epitopes on the same antigen or to two epitopes on different antigens.

In certain embodiments of all aspects and other embodiments of the invention, the bispecific antibody is selected form the group of bispecific antibodies consisting of

- a domain exchanged 1+1 bispecific antibody (CrossMab)
  - (a bispecific, full-length IgG antibody comprising a pair of a first light chain and a first heavy chain comprising a first Fab fragment and a pair of a second light chain and a second heavy chain comprising a second Fab fragment,
  - wherein in the first Fab fragment
    - a) only the CH1 and CL domains are replaced by each other (i.e. the light chain of the first Fab fragment comprises a VL and a CH1 domain and the heavy chain of the first Fab fragment comprises a VH and a CL domain);
    - b) only the VH and VL domains are replaced by each other (i.e. the light chain of the first Fab fragment comprises a VH and a CL domain and the heavy chain of the first Fab fragment comprises a VL and a CH1 domain); or
    - c) the CH1 and CL domains and the VH and VL domains are replaced by each other (i.e. the light chain of the first Fab fragment comprises a VH and a CH1 domain and the heavy chain of the first Fab fragment comprises a VL and a CL domain);
  - wherein the second Fab fragment comprises a light chain comprising a VL and a CL domain, and a heavy chain comprising a VH and a CH1 domain;
  - wherein the first heavy chain and the second heavy chain both comprise a CH3 domain, wherein both CH3 domains are engineered in a complementary manner by respective amino acid substitutions, in order to support heterodimerization of the first heavy chain and the second heavy chain, (in one preferred embodiment, one CH3 domain comprises the knob-mutation and the respective other CH3 domain comprises the hole-mutations);
- C-terminal Fab domain fused 2+1 bispecific antibody (BS)
  - (a bispecific, full length IgG antibody comprising
  - a) one full length antibody comprising two pairs each of a full length antibody light chain and a full length antibody heavy chain, wherein the binding sites formed by each of the pairs of the full length heavy chain and the full length light chain specifically bind to a first antigen, and
  - b) one additional Fab fragment, wherein the additional Fab fragment is fused to the C-terminus of one heavy chain of the full length antibody, wherein the binding site of the additional Fab fragment specifically binds to a second antigen,
  - wherein the additional Fab fragment specifically binding to the second antigen comprises a domain crossover such that a) the light chain variable domain (VL) and the heavy chain variable domain (VH) are replaced by each other, or b) the light chain constant domain (CL) and the heavy chain constant domain (CH1) are replaced by each other);
- a bispecific, one-armed single chain antibody
  - (a bispecific, one-armed single chain antibody comprising a first binding site that specifically binds to a first epitope or antigen and a second binding site that specifically binds to a second epitope or antigen, whereby the individual chains are as follows
    - a light chain (comprising variable light chain domain and light chain constant domain);
    - a combined light/heavy chain (comprising in N- to C-terminal order a variable light chain domain, a light chain constant domain, peptidic linker, variable heavy chain domain, a CH1 domain, a hinge region, a CH2 domain and a CH3 with knob- or hole-mutation)
    - a heavy chain (comprising in N- to C-terminal order a variable heavy chain domain, a CH1 domain, a hinge region, a CH2 domain, a CH3 domain with hole- or knob-mutation));
- a bispecific, two-armed single chain antibody
  - (a bispecific, two-armed single chain antibody comprising a first binding site that specifically binds to a first epitope or antigen and a second binding site that specifically binds to a second epitope or antigen, whereby the individual chains are as follows
    - a combined light/heavy chain 1 (comprising in N- to C-terminal order a variable light chain domain 1, a light chain constant domain, a peptidic linker, a variable heavy chain domain 1, a CH1 domain, a hinge region, a CH2 domain, a CH3 domain with knob- or hole-mutation);

combined light/heavy chain 2 (comprising in N- to C-terminal order a variable light chain domain 2, a light chain constant domain, a peptidic linker, a variable heavy chain domain 2, a CH1 domain, a hinge region, a CH2 domain, a CH3 domain with hole- or knob-mutation));

a common light chain bispecific antibody (a common light chain bispecific antibody comprising a first binding site that specifically binds to a first epitope or antigen and a second binding site that specifically binds to a second epitope or antigen, whereby the individual chains are as follows a light chain (comprising in N- to C-terminal order a variable light chain domain and a light chain constant domain);

a heavy chain 1 (comprising in N- to C-terminal order a variable heavy chain domain 1, a CH1 domain, a hinge region, a CH2 domain, a CH3 domain with hole- or knob-mutation);

heavy chain 2 (comprising in N- to C-terminal order a variable heavy chain domain 2, a CH1 domain, a hinge region, a CH2 domain, a CH3 domain with knob- or hole-mutation));

N-terminal Fab-domain inserted 2+1 bispecific antibody (TCB)

(a bispecific, full-length antibody with additional heavy chain N-terminal binding site with domain exchange comprising a first and a second Fab fragment, wherein each binding site of the first and the second Fab fragment specifically bind to a first antigen, a third Fab fragment, wherein the binding site of the third Fab fragment specifically binds to a second antigen, and wherein the third Fab fragment comprises a domain crossover such that the variable light chain domain (VL) and the variable heavy chain domain (VH) are replaced by each other, and an Fc-region comprising a first Fc-region polypeptide and a second Fc-region polypeptide, wherein the first and the second Fab fragment each comprise a heavy chain fragment and a full-length light chain, wherein the C-terminus of the heavy chain fragment of the first Fab fragment is fused to the N-terminus of the first Fc-region polypeptide, wherein the C-terminus of the heavy chain fragment of the second Fab fragment is fused to the N-terminus of the variable light chain domain of the third Fab fragment and the C-terminus of the CH1 domain of the third Fab fragment is fused to the N-terminus of the second Fc-region polypeptide);

an antibody-multimer-fusion (fusion polypeptide comprising (a) an antibody heavy chain and an antibody light chain, and (b) a first fusion polypeptide comprising in N- to C-terminal direction a first part of a non-antibody multimeric polypeptide, an antibody heavy chain CH1 domain or an antibody light chain constant domain, an antibody hinge region, an antibody heavy chain CH2 domain and an antibody heavy chain CH3 domain, and a second fusion polypeptide comprising in N- to C-terminal direction the second part of the non-antibody multimeric polypeptide and an antibody light chain constant domain if the first polypeptide comprises an antibody heavy chain CH1 domain or an antibody heavy chain CH1 domain if the first polypeptide comprises an antibody light chain constant domain, wherein (i) the antibody heavy chain of (a) and the first fusion polypeptide of (b), (ii) the antibody heavy chain of (a) and the antibody light chain of (a), and (iii) the first fusion polypeptide of (b) and the second fusion polypeptide of (b) are each independently of each other covalently linked to each other by at least one disulfide bond, wherein the variable domains of the antibody heavy chain and the antibody light chain form a binding site specifically binding to an antigen).

The CH3 domains in the heavy chains of an antibody can be altered by the "knob-into-holes" technology, which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method, the interaction surfaces of the two CH3 domains are altered to increase the heterodimerization of these two CH3 domains and thereby of the polypeptide comprising them. Each of the two CH3 domains (of the two heavy chains) can be the "knob", while the respective other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

The mutation T366W in the CH3 domain (of an antibody heavy chain) is denoted as "knob-mutation" and the mutations T366S, L368A, Y407V in the CH3 domain (of an antibody heavy chain) are denoted as "hole-mutations" (numbering according to Kabat EU index). An additional inter-chain disulfide bridge between the CH3 domains can also be used (Merchant, A. M., et al., Nature Biotech. 16 (1998) 677-681) e.g. by introducing a S354C mutation into the CH3 domain of the heavy chain with the "knob-mutation" (denotes as "knob-cys-mutations") and by introducing a Y349C mutation into the CH3 domain of the heavy chain with the "hole-mutations" (denotes as "hole-cys-mutations") (numbering according to Kabat EU index).

The term "domain crossover" as used herein denotes that in a pair of an antibody heavy chain VH—CH1 fragment and its corresponding cognate antibody light chain, i.e. in an antibody Fab (fragment antigen binding), the domain sequence deviates from the sequence in a native antibody in that at least one heavy chain domain is substituted by its corresponding light chain domain and vice versa. There are three general types of domain crossovers, (i) the crossover of the CH1 and the CL domains, which leads by the domain crossover in the light chain to a VL-CH1 domain sequence and by the domain crossover in the heavy chain fragment to a VH-CL domain sequence (or a full length antibody heavy chain with a VH-CL-hinge-CH2-CH3 domain sequence), (ii) the domain crossover of the VH and the VL domains, which leads by the domain crossover in the light chain to a VH-CL domain sequence and by the domain crossover in the heavy chain fragment to a VL-CH1 domain sequence, and (iii) the domain crossover of the complete light chain (VL-CL) and the complete VH—CH1 heavy chain fragment ("Fab crossover"), which leads to by domain crossover to a light chain with a VH—CH1 domain sequence and by domain crossover to a heavy chain fragment with a VL-CL domain sequence (all aforementioned domain sequences are indicated in N-terminal to C-terminal direction).

As used herein the term "replaced by each other" with respect to corresponding heavy and light chain domains refers to the aforementioned domain crossovers. As such, when CH1 and CL domains are "replaced by each other" it is referred to the domain crossover mentioned under item (i) and the resulting heavy and light chain domain sequence. Accordingly, when VH and VL are "replaced by each other" it is referred to the domain crossover mentioned under item (ii); and when the CH1 and CL domains are "replaced by each other" and the VH and VL domains are "replaced by each other" it is referred to the domain crossover mentioned under item (iii). Bispecific antibodies including domain crossovers are reported, e.g. in WO 2009/080251, WO 2009/080252, WO 2009/080253, WO 2009/080254 and Schaefer, W., et al, Proc. Natl. Acad. Sci. USA 108 (2011) 11187-11192. Such antibodies are generally termed CrossMab.

Multispecific antibodies also comprise, in certain embodiments of all aspects and other embodiments of the invention, at least one Fab fragment including either a domain crossover of the CH1 and the CL domains as mentioned under item (i) above, or a domain crossover of the VH and the VL domains as mentioned under item (ii) above, or a domain crossover of the VH—CH1 and the VL-VL domains as mentioned under item (iii) above. In case of multispecific antibodies with domain crossover, the Fabs specifically binding to the same antigen(s) are constructed, in certain embodiments, to be of the same domain sequence. Hence, in case more than one Fab with a domain crossover is contained in the multispecific antibody, said Fab(s) specifically bind to the same antigen.

The term "recombinant antibody", as used herein, denotes all antibodies (chimeric, humanized and human) that are prepared, expressed, created or isolated by recombinant means, such as recombinant cells. This includes antibodies isolated from recombinant cells such as NS0, HEK, BHK, amniocyte or CHO cells.

As used herein, the term "antibody fragment" refers to a molecule other than an intact antibody that comprises a portion of an intact antibody that binds the antigen to which the intact antibody binds, i.e. it is a functional fragment. Examples of antibody fragments include but are not limited to Fv; Fab; Fab'; Fab'-SH; F(ab')2; bispecific Fab; diabodies; linear antibodies; single-chain antibody molecules (e.g., scFv or scFab).

Recombinant Methods

Antibodies may be produced using recombinant methods and compositions, e.g., as described in U.S. Pat. No. 4,816,567. For these methods, one or more isolated nucleic acid(s) encoding an antibody are provided.

In one aspect of the invention, a method of producing an antibody is provided, wherein the method comprises culturing a cell clone comprising nucleic acid(s) encoding the antibody, under conditions suitable for expression of the antibody, and optionally recovering the antibody from the host cell (or host cell culture medium), wherein the cell clone has been selected with a method according to the current invention.

For recombinant production of an antibody, nucleic acids encoding the antibody are generated/designed/synthesized and inserted into one or more vectors for further cloning and/or expression in a cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Generally, for the recombinant large-scale production of a polypeptide of interest, such as e.g. a therapeutic antibody, a cell clone stably expressing and secreting said polypeptide is required. This cell clone is termed "recombinant cell clone" or "recombinant production cell clone" and the overall process used for generating such a cell is termed "cell line development". In the first step of the cell line development process, a suitable host cell, such as e.g., in certain embodiments, a CHO cell, is transfected with one or more nucleic acid sequences suitable for expression of said polypeptide of interest. In a second step, cell clones stably expressing the polypeptide of interest are selected based on the co-expression of a selection marker, which had been co-transfected with the nucleic acids encoding the polypeptide of interest.

A nucleic acid encoding a polypeptide, i.e. the coding sequence, is denoted as a structural gene. Such a structural gene is pure coding information. Thus, additional regulatory elements are required for expression thereof. Therefore, normally a structural gene is integrated in a so-called expression cassette. The minimal regulatory elements needed for an expression cassette to be functional in a mammalian cell are a promoter functional in said mammalian cell, which is located upstream, i.e. 5', to the structural gene, and a polyadenylation signal sequence functional in said mammalian cell, which is located downstream, i.e. 3', to the structural gene. The promoter, the structural gene and the polyadenylation signal sequence are arranged in an operably linked form.

In case the polypeptide of interest is a heteromultimeric polypeptide that is composed of different polypeptides, such as e.g. an antibody or a complex antibody format, not only a single expression cassette is required but a multitude of expression cassettes differing in the respectively contained structural gene, i.e. at least one expression cassette for each of the different polypeptides (chains) of the heteromultimeric polypeptide (heteromultimeric antibody). For example, a full-length antibody is a heteromultimeric polypeptide comprising two copies of a light chain as well as two copies of a heavy chain. Thus, a full-length antibody is composed of two different polypeptides. Therefore, two expression cassettes are required for the expression of a full-length antibody, one for the light chain and one for the heavy chain. If, for example, the full-length antibody is a bispecific antibody, i.e. the antibody comprises two different binding sites specifically binding to two different antigens/epitopes on the same antigen, the two light chains as well as the two heavy chains are also different from each other. Thus, such a bispecific, full-length antibody is composed of four different polypeptides and therefore, four expression cassettes are required.

The expression cassette(s) for the polypeptide of interest is(are) in turn integrated into one or more so called "expression vector(s)". An "expression vector" is a nucleic acid providing all required elements for the amplification of said vector in bacterial cells as well as the expression of the comprised structural gene(s) in a mammalian cell. Typically, an expression vector comprises a prokaryotic plasmid propagation unit, e.g. for *E. coli*, comprising an origin of replication, and a prokaryotic selection marker, as well as a eukaryotic selection marker, and the expression cassettes required for the expression of the structural gene(s) of interest. An "expression vector" is a transport vehicle for the introduction of expression cassettes into a mammalian host cell to generate polypeptide-expressing cell clones.

As outlined in the previous paragraphs, the more complex the polypeptide to be expressed is, the higher also the number of required different expression cassettes will be. Inherently with the number of expression cassettes also the size of the nucleic acid to be integrated into the genome of the host cell increases. Concomitantly also the size of the expression vector increases. However, there is a practical upper limit to the size of a vector in the range of about 15 kbps above which handling and processing efficiency profoundly drops. This issue can be addressed by using two or more expression vectors. Thereby the expression cassettes can be split between different expression vectors each comprising only some of the expression cassettes resulting in a size reduction.

Cell line development (CLD) for the generation of recombinant cell expressing a heterologous polypeptide, such as e.g. a multispecific antibody, employs either random integration (RI) or targeted integration (TI) of the nucleic acid(s) comprising the respective expression cassettes required for the expression and production of the heterologous polypeptide of interest.

Using RI, in general, several vectors or fragments thereof integrate into the cell's genome at the same or different loci.

Using TI, in general, a single copy of the transgene comprising the different expression cassettes is integrated at a predetermined "hot-spot" in the host cell's genome.

Suitable host cells for the generation of cell clones for expression of an (glycosylated) antibody are generally derived from multicellular organisms such as e.g. vertebrates.

Host Cells

Any mammalian host cell line that is adapted to grow in suspension can be used to generate recombinant cell clones that can be processed in the method according to the current invention. In addition, independent from the integration method, i.e. for RI as well as TI, any mammalian host cell can be used.

Examples of useful mammalian host cell lines are human amniocyte cells (e.g. CAP-T cells as described in Woelfel, J. et al., BMC Proc. 5 (2011) P133); monkey kidney CV1 line transformed by SV40 (COS-7); human embryonic kidney line (HEK293 or HEK293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In certain embodiments of all aspects and other embodiments of the invention, the mammalian host cell is, e.g., a Chinese Hamster Ovary (CHO) cell (e.g. CHO K1, CHO DG44, etc.), a Human Embryonic Kidney (HEK) cell, a lymphoid cell (e.g., Y0, NS0, Sp2/0 cell), or a human amniocyte cells (e.g. CAP-T, etc.). In one preferred embodiment, the mammalian (host) cell is a CHO cell. Thus, likewise the cell clone is a CHO cell.

With respect to TI, any known or future mammalian host cell suitable for TI comprising a landing site as described herein integrated at a single site within a locus of the genome can be used in the current invention. Such a cell is denoted as mammalian TI host cell. In certain embodiments, the mammalian TI host cell is a hamster cell, a human cell, a rat cell, or a mouse cell comprising a landing site as described herein. In one preferred embodiment, the mammalian TI host cell is a CHO cell. In certain embodiments, the mammalian TI host cell is a Chinese hamster ovary (CHO) cell, a CHO K1 cell, a CHO K1SV cell, a CHO DG44 cell, a CHO DUKXB-11 cell, a CHO K1S cell, or a CHO K1M cell comprising a landing site as described herein integrated at a single site within a locus of the genome.

In certain embodiments of all aspects and other embodiments of the invention, a mammalian TI host cell comprises an integrated landing site, wherein the landing site comprises one or more recombination recognition sequence (RRS). The RRS can be recognized by a recombinase, for example, a Cre recombinase, an FLP recombinase, a Bxb1 integrase, or a φC31 integrase. The RRS can be selected independently of each other from the group consisting of a LoxP sequence, a LoxP L3 sequence, a LoxP 2 L sequence, a LoxFas sequence, a Lox511 sequence, a Lox2272 sequence, a Lox2372 sequence, a Lox5171 sequence, a Loxm2 sequence, a Lox71 sequence, a Lox66 sequence, a FRT sequence, a Bxb1 attP sequence, a Bxb1 attB sequence, a φC31 attP sequence, and a φC31 attB sequence. If multiple RRSs have to be present, the selection of each of the sequences is dependent on the other insofar as non-identical RRSs are chosen.

Although the invention is exemplified with a CHO cell hereafter, this is presented solely to exemplify the invention but shall not be construed in any way as limitation. The true scope of the invention is set forth in the claims.

Targeted Integration

One method for the generation of a recombinant mammalian cell clone to be processed in the method according to the current invention is a recombinant cell clone generated by using targeted integration (TI) for the introduction of the coding nucleic acid.

In targeted integration, site-specific recombination is employed for the introduction of an exogenous nucleic acid into a specific locus in the genome of a mammalian TI host cell to generate recombinant cell clones. This is an enzymatic process wherein a sequence at the site of integration in the genome is exchanged for the exogenous nucleic acid. One system used to effect such nucleic acid exchanges is the Cre-lox system. The enzyme catalyzing the exchange is the Cre recombinase. The sequence to be exchanged is defined by the position of two lox(P)-sites in the genome as well as in the exogenous nucleic acid. These lox(P)-sites are recognized by the Cre recombinase. Nothing more is required, i.e. no ATP etc. Originally, the Cre-lox system has been found in bacteriophage P1.

The Cre-lox system operates in different cell types, like mammals, plants, bacteria and yeast.

In certain embodiments of all aspects and other embodiments of the current invention, the exogenous nucleic acid encoding the heterologous polypeptide has been integrated into the mammalian TI host cell by single or double recombinase mediated cassette exchange (RMCE). Thereby a recombinant mammalian cell clone, such as a recombinant CHO cell clone, is obtained, in which a defined and specific expression cassette sequence has been integrated into the genome at a single locus.

The Cre-LoxP site-specific recombination system has been widely used in many biological experimental systems. Cre recombinase is a 38-kDa site-specific DNA recombinase that recognizes 34 bp LoxP sequences. Cre recombinase is derived from bacteriophage P1 and belongs to the tyrosine family site-specific recombinase. Cre recombinase can mediate both intra and intermolecular recombination between LoxP sequences. The LoxP sequence is composed of an 8 bp non-palindromic core region flanked by two 13 bp inverted repeats. Cre recombinase binds to the 13 bp repeat thereby mediating recombination within the 8 bp core region. Cre-LoxP-mediated recombination occurs at a high efficiency and does not require any other host factors. If two LoxP sequences are placed in the same orientation on the same nucleotide sequence, Cre recombinase-mediated recombination will excise DNA sequences located between the two LoxP sequences as a covalently closed circle. If two LoxP sequences are placed in an inverted position on the same nucleotide sequence, Cre recombinase-mediated recombination will invert the orientation of the DNA sequences located between the two sequences. If two LoxP sequences are on two different DNA molecules and if one DNA molecule is circular, Cre recombinase-mediated recombination will result in integration of the circular DNA sequence.

A "recombination recognition sequence" (RRS) is a nucleotide sequence recognized by a recombinase and is necessary and sufficient for recombinase-mediated recombination events. A RRS can be used to define the position where a recombination event will occur in a nucleotide sequence.

The term "matching RRSs" indicates that a recombination occurs between two RRSs. In certain embodiments, the two matching RRSs are the same.

In certain embodiments of all aspects and other embodiments of the current invention, a RRS can be recognized by a Cre recombinase. In certain embodiments, a RRS can be recognized by a FLP recombinase. In certain embodiments, a RRS can be recognized by a Bxb1 integrase. In certain embodiments, a RRS can be recognized by a φC31 integrase.

In certain embodiments of all aspects and other embodiments of the current invention, both RRSs are wild-type LoxP sequences. In certain embodiments, both RRSs are mutant LoxP sequences. In certain embodiments, both RRSs are wild-type FRT sequences. In certain embodiments, both RRSs are mutant FRT sequences. In certain embodiments, the two matching RRSs are different sequences but can be recognized by the same recombinase. In certain embodiments, the first matching RRS is a Bxb1 attP sequence and the second matching RRS is a Bxb1 attB sequence. In certain embodiments, the first matching RRS is a φC31 attB sequence and the second matching RRS is a φC31 attB sequence.

A "two-plasmid RMCE" strategy or "double RMCE" is employed in the method according to the current invention when using a two-vector combination. For example, but not by way of limitation, an integrated landing site could comprise three RRSs, e.g., an arrangement where the third RRS ("RRS3") is present between the first RRS ("RRS1") and the second RRS ("RRS2"), while a first vector comprises two RRSs matching the first and the third RRS on the integrated exogenous nucleotide sequence, and a second vector comprises two RRSs matching the third and the second RRS on the integrated exogenous nucleotide sequence.

The two-plasmid RMCE strategy involves using three RRS sites to carry out two independent RMCEs simultaneously. Therefore, a landing site in the mammalian TI host cell using the two-plasmid RMCE strategy includes a third RRS site (RRS3) that has no cross activity with either the first RRS site (RRS1) or the second RRS site (RRS2). The two plasmids to be targeted require the same flanking RRS sites for efficient targeting, one plasmid (front) flanked by RRS1 and RRS3 and the other (back) by RRS3 and RRS2. In addition, two selection markers are needed in the two-plasmid RMCE. One selection marker expression cassette was split into two parts. The front plasmid would contain the promoter followed by a start codon and the RRS3 sequence. The back plasmid would have the RRS3 sequence fused to the N-terminus of the selection marker coding region, minus the start-codon (ATG). Additional nucleotides may need to be inserted between the RRS3 site and the selection marker sequence to ensure in frame translation for the fusion protein, i.e. operable linkage. Only when both plasmids are correctly inserted, the full expression cassette of the selection marker will be assembled and, thus, rendering cells resistance to the respective selection agent.

Two-plasmid RMCE involves double recombination crossover events, catalyzed by a recombinase, between the two heterospecific RRSs within the target genomic locus and the donor DNA molecule. Two-plasmid RMCE is designed to introduce a copy of the DNA sequences from the front- and back-vector in combination into the predetermined locus of a mammalian TI host cell's genome. RMCE can be implemented such that prokaryotic vector sequences are not introduced into the mammalian TI host cell's genome, thus, reducing and/or preventing unwanted triggering of host immune or defense mechanisms. The RMCE procedure can be repeated with multiple DNA sequences.

In certain embodiments of all aspects and other embodiments of the current invention, targeted integration is achieved by two RMCEs, wherein two different DNA sequences, each comprising at least one expression cassette encoding a part of a heteromultimeric polypeptide and/or at least one selection marker or part thereof flanked by two heterospecific RRSs, are both integrated into a predetermined site of the genome of a RRSs matching mammalian TI host cell. In certain embodiments, targeted integration is achieved by multiple RMCEs, wherein DNA sequences from multiple vectors, each comprising at least one expression cassette encoding a part of a heteromultimeric polypeptide and/or at least one selection marker or part thereof flanked by two heterospecific RRSs, are all integrated into a predetermined site of the genome of a mammalian TI host cell. In certain embodiments, the selection marker can be partially encoded on the first vector and partially encoded on the second vector such that only the correct integration of both by double RMCE allows for the expression of the selection marker.

In certain embodiments of all aspects and other embodiments of the current invention, targeted integration via recombinase-mediated recombination leads to selection marker and/or the different expression cassettes for the multimeric polypeptide integrated into one or more predetermined integration sites of a host cell genome free of sequences from a prokaryotic vector.

An exemplary mammalian TI host cell that is suitable for use in a method according to the current invention is a CHO cell harboring a landing site integrated at a single site within a locus of its genome wherein the landing site comprises three heterospecific loxP sites for Cre recombinase mediated DNA recombination.

In this example, the heterospecific loxP sites are L3, LoxFas and 2 L (see e.g. Lanza et al., Biotechnol. J. 7 (2012)

898-908; Wong et al., Nucleic Acids Res. 33 (2005) e147), whereby L3 and 2 L flank the landing site at the 5'-end and 3'-end, respectively, and LoxFas is located between the L3 and 2 L sites. The landing site further contains a bicistronic unit linking the expression of a selection marker via an IRES to the expression of the fluorescent GFP protein allowing to stabilize the landing site by positive selection as well as to select for the absence of the site after transfection and Cre-recombination (negative selection). Green fluorescence protein (GFP) serves for monitoring the RMCE reaction.

Such a configuration of the landing site as outlined in the previous paragraph allows for the simultaneous integration of two vectors, e.g. of a so called front vector harboring an L3 and a LoxFas site and a back vector harboring a LoxFas and an 2 L site. The functional elements of a selection marker gene different from that present in the landing site can be distributed between both vectors: promoter and start codon can be located on the front vector whereas coding region and polyadenylation signal sequence are located on the back vector. Only correct recombinase-mediated integration of said nucleic acids from both vectors induces resistance against the respective selection agent.

Generally, a mammalian TI host cell is a mammalian cell comprising a landing site integrated at a single site within a locus of the genome of the mammalian cell, wherein the landing site comprises a first and a second recombination recognition sequence flanking at least one first selection marker, and a third recombination recognition sequence located between the first and the second recombination recognition sequence, and all the recombination recognition sequences are different.

The selection marker(s) can be selected from the group consisting of an aminoglycoside phosphotransferase (APH) (e.g., hygromycin phosphotransferase (HYG), neomycin and G418 APH), dihydrofolate reductase (DHFR), thymidine kinase (TK), glutamine synthetase (GS), asparagine synthetase, tryptophan synthetase (indole), histidinol dehydrogenase (histidinol D), and genes encoding resistance to puromycin, blasticidin, bleomycin, phleomycin, chloramphenicol, Zeocin, and mycophenolic acid. The selection marker(s) can also be a fluorescent protein selected from the group consisting of green fluorescent protein (GFP), enhanced GFP (eGFP), a synthetic GFP, yellow fluorescent protein (YFP), enhanced YFP (eYFP), cyan fluorescent protein (CFP), mPlum, mCherry, tdTomato, mStrawberry, J-red, DsRed-monomer, mOrange, mKO, mCitrine, Venus, YPet, Emerald6, CyPet, mCFPm, Cerulean, and T-Sapphire.

An exogenous nucleotide sequence is a nucleotide sequence that does not originate from a specific cell but can be introduced into said cell by DNA delivery methods, such as, e.g., by transfection, electroporation, or transformation methods. In certain embodiments, a mammalian TI host cell comprises at least one landing site integrated at one or more integration sites in the mammalian cell's genome. In certain embodiments, the landing site is integrated at one or more integration sites within a specific locus of the genome of the mammalian cell.

In certain embodiments of all aspects and other embodiments of the current invention, the integrated landing site comprises at least one selection marker. In certain embodiments, the integrated landing site comprises a first, a second and a third RRS, and at least one selection marker. In certain embodiments, a selection marker is located between the first and the second RRS. In certain embodiments, two RRSs flank at least one selection marker, i.e., a first RRS is located 5' (upstream) and a second RRS is located 3' (downstream) of the selection marker. In certain embodiments, a first RRS is adjacent to the 5'-end of the selection marker and a second RRS is adjacent to the 3'-end of the selection marker. In certain embodiments, the landing site comprises a first, second, and third RRS, and at least one selection marker located between the first and the third RRS.

In certain embodiments of all aspects and other embodiments of the current invention, a selection marker is located between a first and a second RRS and the two flanking RRSs are different. In certain preferred embodiments, the first flanking RRS is a LoxP L3 sequence and the second flanking RRS is a LoxP 2 L sequence. In certain embodiments, a LoxP L3 sequence is located 5' of the selection marker and a LoxP 2 L sequence is located 3' of the selection marker. In certain embodiments, the first flanking RRS is a wild-type FRT sequence and the second flanking RRS is a mutant FRT sequence. In certain embodiments, the first flanking RRS is a Bxb1 attP sequence and the second flanking RRS is a Bxb1 attB sequence. In certain embodiments, the first flanking RRS is a φC31 attP sequence and the second flanking RRS is a φC31 attB sequence. In certain embodiments, the two RRSs are positioned in the same orientation. In certain embodiments, the two RRSs are both in the forward or reverse orientation. In certain embodiments, the two RRSs are positioned in opposite orientations.

In certain embodiments of all aspects and other embodiments of the current invention, the integrated landing site comprises a first and a second selection marker, which are flanked by two RRSs, wherein the first selection marker is different from the second selection marker. In certain embodiments, the two selection markers are both independently of each other selected from the group consisting of a glutamine synthetase selection marker, a thymidine kinase selection marker, a HYG selection marker, and a puromycin resistance selection marker. In certain embodiments, the integrated landing site comprises a thymidine kinase selection marker and a HYG selection marker. In certain embodiments, the first selection maker is selected from the group consisting of an aminoglycoside phosphotransferase (APH) (e.g., hygromycin phosphotransferase (HYG), neomycin and G418 APH), dihydrofolate reductase (DHFR), thymidine kinase (TK), glutamine synthetase (GS), asparagine synthetase, tryptophan synthetase (indole), histidinol dehydrogenase (histidinol D), and genes encoding resistance to puromycin, blasticidin, bleomycin, phleomycin, chloramphenicol, Zeocin, and mycophenolic acid, and the second selection maker is selected from the group consisting of a GFP, an eGFP, a synthetic GFP, a YFP, an eYFP, a CFP, an mPlum, an mCherry, a tdTomato, an mStrawberry, a J-red, a DsRed-monomer, an mOrange, an mKO, an mCitrine, a Venus, a YPet, an Emerald, a CyPet, an mCFPm, a Cerulean, and a T-Sapphire fluorescent protein. In certain embodiments, the first selection marker is a glutamine synthetase selection marker and the second selection marker is a GFP fluorescent protein. In certain embodiments, the two RRSs flanking both selection markers are different.

In certain embodiments of all aspects and other embodiments of the current invention, the selection marker is operably linked to a promoter sequence. In certain embodiments, the selection marker is operably linked to an SV40 promoter. In certain embodiments, the selection marker is operably linked to a human Cytomegalovirus (CMV) promoter.

Lipases

Lipases (EC 3.1.1.x) belong to the family of hydrolases, which occur in animals, plants, and microorganisms and cleave carboxylic acid esters. Their natural function is to hydrolyze triglycerides into diglycerides, monoglycerides, fatty acids, and glycerol. This is called lipolysis. Lipases are not restricted to the hydrolysis of triglycerides (this is only true for triacylglycerol lipase, 3.1.1.3). There are also other lipase families, such as phospholipases (3.1.1.32), which hydrolyze other substrates (e.g. phospholipids). All of these are deemed associated with polysorbate degradation.

Lipolysis is an enzymatic reaction and, thus, an equilibrium reaction.

Lipases operate at the lipid/water interface, and are only slightly active in the absence of this boundary layer [7, 8]. The activity of most lipases increases significantly when they come into contact with a non-polar fat droplet or a micelle in an aqueous medium, what is termed interface activation [9], and are collocated specifically at these interfaces.

An important feature of some lipases is the presence of a movable structural element, the lid or flap, which is located above the enzymatically active site. When the so-called "lid" is closed, the active site is protected from the environment and is inaccessible to substrates, so that the lipase is inactive. In the open conformation, substrates can access the active site and undergo enzymatic transformation.

Lipases have a rather low catalytic activity in an aqueous medium and show a higher catalytic activity in organic media [10].

The term "hydrolase" is used herein in the broadest sense and refers to a molecule/compound with hydrolytic activity. Generally, a "hydrolase" is thus an enzyme that hydrolyzes a chemical bond. For example, a "hydrolase" is a carboxylic derived ester-cleaving enzyme, which has final products the derived free carboxylic acid and the corresponding alcohol. Alternatively, a hydrolase is an enzyme exhibiting hydrolase activity, i.e. breaking covalent bond by using a water molecule. Non-limiting examples of a "hydrolase" are a lipase, an esterase, a thioesterase, a phospholipase or a ceramidase.

"Hydrolytic activity" as used herein as known in the art and refers to the ability to hydrolyze chemical bonds. Hydrolysis refers to the cleavage of a chemical bond in which a water molecule acts as a nucleophile. Preferably, the molecule/compound with hydrolytic activity is a protein or a polypeptide with hydrolytic activity.

Accordingly, the protein or polypeptide with hydrolytic activity is an enzyme with hydrolytic activity. Thus, the hydrolase is an enzyme with hydrolytic activity. The hydrolase may be an esterase or an amidase.

The term "esterase" is well known in the art and refers in context of this invention to an enzyme that catalyzes the hydrolysis of an ester bond to create an acid and an alcohol. In other words, an esterase may act on (an) ester bond. Esterases are a diverse category of enzymes, including acetyl esterases, phosphatases, nucleases, thioesterases, and carboxylic ester hydrolases.

A carboxylic ester hydrolase uses a water molecule to hydrolyze a carboxylic ester into an alcohol and a carboxylate. Most preferably, a hydrolase/esterase (such as a carboxylic ester hydrolase) is a lipase. A lipase catalyzes the hydrolysis of fatty acid esters/lipids, including triglycerides, fats and oils into fatty acids and an alcohol head group.

In certain embodiments of all aspects and other embodiments of the current invention, (a) hydrolase(s) of the methods according to the invention is Lipoprotein Lipase (Accession number: G3H6V7), Palmitoyl Proteinthioesterase 1 (Accession number: G3HN89), Acid Ceramidase (Accession number: G3GZB2), the C-terminal domain of Fatty Acid synthase (Accession number: G3GXD7), Putative Phospholipase b-like 2 (Accession number: G316T1), Lysosomal Acid Lipase (Accession number: G3HQY6), Lysosomal Phospholipase, Phospholipase A2, group VII (PLA2G7) and group XV (PLA2G15), Sialate O-Acetylesterase.

In certain embodiments of all aspects and other embodiments of the current invention, (a) hydrolase(s) of the method according to the invention is Lipoprotein Lipase, Putative Phospholipase b-like 2, and/or Lysosomal Phospholipase. This is because of their documented hydrolase activity towards surfactants, such as polysorbate, which is attributed to the formation of (visible) particles in compositions and/or decreased stability of compositions.

In certain embodiments of all aspects and other embodiments of the current invention, the hydrolase(s) of the method according to the invention is Lysosomal Phospholipase, specifically lysosomal phospholipase A2 (LPLA2) (Accession number: G3HKV9).

In certain embodiments of all aspects and other embodiments of the invention, the hydrolase/hydrolase activity, i.e. hydrolytic activity, is based on the presence of one or more hydrolase(s) selected from the group consisting of Lipoprotein Lipase, Palmitoyl Proteinthioesterase, Acid Ceramidase, the C-terminal domain of Fatty Acid synthase, Putative Phospholipase b-like 2, Lysosomal Acid Lipase, Lysosomal Phospholipase, and Sialate O-Acetylesterase.

In certain embodiments of all aspects and embodiments of the invention, the hydrolase is selected from the group consisting of Lipoprotein Lipase, Palmitoyl Proteinthioesterase, Acid Ceramidase, the C-terminal domain of Fatty Acid synthase, Putative Phospholipase b-like 2, Lysosomal Acid Lipase, Lysosomal Phospholipase and Sialate O-Acetylesterase.

Nucleic Acid Tags

An "oligonucleotide" is a short single stranded nucleic-acid usually consisting of up to approximately 15 nucleotide monomers which are connected by phosphodiester bonds between the 3' carbon atom of one sugar molecule and the 5' carbon atom of another. The monomers comprised in an oligonucleotide (in a generic sense) can not only be naturally occurring monomers but also non-naturally occurring monomers, also referred to as nucleotide analogs. In a non-limiting way, exemplary analogs comprise sugar moieties other than ribose or deoxyribose, particularly a ribose in which the ring of the sugar is "locked" by a methylene bridge connecting the 2'-O atom and the 4'-C atom. For the purpose of the present disclosure, the term nucleotide encompasses naturally and non-naturally occurring nucleotides as monomers in an oligonucleotide. Thus, an oligonucleotide according to this definition can be composed of naturally or non-naturally occurring monomers exclusively, or it can be composed of a mixture thereof. In addition, it is understood that different classes of non-naturally occurring monomers (e.g. PNA, D-LNA, L-LNA, homo-DNA (with hexose sugar), HNA (with hexitol sugar, hexitol nucleic acid), L-DNA, etc.) can be comprised in an oligonucleotide, if not stated otherwise.

In certain embodiments of all aspects and other embodiments of the current invention, the immobilization tag is a nucleic acid tag.

A nucleic acid tag is one member of a binding pair of two separate compatible nucleic acid partners, i.e. complementary nucleic acid sequences.

In certain embodiments of all aspects and other embodiments of the current invention, the immobilization tag is a nucleic acid tag consisting of LNA oligonucleotides.

Several such single-stranded all-LNA oligonucleotides have been found and are exemplary embodiments of said nucleic acid sequence tag, i.e. non-limiting examples illustrating oligonucleotides that are capable of being used as immobilization tag as they can bind to other complementary sequences by way of hybridization and duplex formation, under non-denaturing conditions. The following list provides a non-limiting compilation thereof. It is understood that the listed sequences denote all-LNA nucleosides, i.e. oligonucleotides containing only LNA monomers. Sequences are given in the conventional orientation, i.e. from the 5' terminus to the 3' terminus. The sequences are paired, i.e. two successive sequences can be used as hybridizing pair, whereof one is the nucleic acid tag on the artificial substrate and the other is bound to the solid phase for capturing.

In certain embodiments of all aspects and other embodiments of the invention, the nucleic acid sequence tag is selected from the group consisting of

```
SEQ ID NO: 01: tgctcctg;
SEQ ID NO: 02: caggagca;
SEQ ID NO: 09: tgctcctgt;
SEQ ID NO: 10: acaggagca;
SEQ ID NO: 11: gtgcgtct;
SEQ ID NO: 12: agacgcac;
SEQ ID NO: 13: gttggtgt;
SEQ ID NO: 14: acaccaac;
SEQ ID NO: 33: cttcc;
SEQ ID NO: 34: ggaag;
SEQ ID NO: 42: gctcc;
SEQ ID NO: 43: ggagc;
SEQ ID NO: 16: gttggt;
SEQ ID NO: 46: ccaac;
SEQ ID NO: 16: gttggt;
SEQ ID NO: 19: caccaac;
SEQ ID NO: 16: gttggt;
SEQ ID NO: 17: caacacaccaac;
SEQ ID NO: 16: gttggt;
SEQ ID NO: 18: acacaccaac;
SEQ ID NO: 16: gttggt;
SEQ ID NO: 14: acaccaac;
SEQ ID NO: 16: gttggt;
SEQ ID NO: 20: accaac;
SEQ ID NO: 40: ctgtca;
SEQ ID NO: 41: tgacag;
SEQ ID NO: 44: tgctcc;
SEQ ID NO: 45: ggagca;
SEQ ID NO: 35: tcttcc;
SEQ ID NO: 36: ggaaga;
```

-continued

```
SEQ ID NO: 21: gttggtg;
SEQ ID NO: 17: caacacaccaac;
SEQ ID NO: 21: gttggtg;
SEQ ID NO: 18: acacaccaac;
SEQ ID NO: 21: gttggtg;
SEQ ID NO: 14: acaccaac;
SEQ ID NO: 21: gttggtg;
SEQ ID NO: 19: caccaac;
SEQ ID NO: 21: gttggtg;
SEQ ID NO: 20: accaac;
SEQ ID NO: 01: tgctcctg;
SEQ ID NO: 02: caggagca;
SEQ ID NO: 11: gtgcgtct;
SEQ ID NO: 12: agacgcac;
SEQ ID NO: 13: gttggtgt;
SEQ ID NO: 17: caacacaccaac;
SEQ ID NO: 13: gttggtgt;
SEQ ID NO: 18: acacaccaac;
SEQ ID NO: 13: gttggtgt;
SEQ ID NO: 14: acaccaac;
SEQ ID NO: 13: gttggtgt;
SEQ ID NO: 19: caccaac;
SEQ ID NO: 13: gttggtgt;
SEQ ID NO: 20: accaac;
SEQ ID NO: 22: gttggtgtg;
SEQ ID NO: 17: caacacaccaac;
SEQ ID NO: 22: gttggtgtg;
SEQ ID NO: 18: acacaccaac;
SEQ ID NO: 22: gttggtgtg;
SEQ ID NO: 14: acaccaac;
SEQ ID NO: 22: gttggtgtg;
SEQ ID NO: 19: caccaac;
SEQ ID NO: 22: gttggtgtg;
SEQ ID NO: 20: accaac;
SEQ ID NO: 09: tgctcctgt;
SEQ ID NO: 15: caggagc;
SEQ ID NO: 09: tgctcctgt;
SEQ ID NO: 10: acaggagca;
SEQ ID NO: 09: tgctcctgt;
SEQ ID NO: 02: caggagca;
SEQ ID NO: 22: gttggtgtg;
```

-continued

```
SEQ ID NO: 30: cacaccaac;

SEQ ID NO: 37: ttctcttcc;

SEQ ID NO: 38: ggaagagaa;

SEQ ID NO: 23: gttggtgtgttg;

SEQ ID NO: 17: caacacaccaac;

SEQ ID NO: 23: gttggtgtgttg;

SEQ ID NO: 18: acacaccaac;

SEQ ID NO: 23: gttggtgtgttg;

SEQ ID NO: 14: acaccaac;

SEQ ID NO: 23: gttggtgtgttg;

SEQ ID NO: 19: caccaac;

SEQ ID NO: 23: gttggtgtgttg:

SEQ ID NO: 20: accaac;

SEQ ID NO: 31: gttggtgtgttggtg;

SEQ ID NO: 32: caccaacacaccaac;

SEQ ID NO: 28: aaaaaaaaa;

SEQ ID NO: 24: ttttttttt;

SEQ ID NO: 28: aaaaaaaaa;

SEQ ID NO: 25: tttttttt;

SEQ ID NO: 28: aaaaaaaaa;

SEQ ID NO: 26: tttttt;

SEQ ID NO: 28: aaaaaaaaa;

SEQ ID NO: 27: tttttt;

SEQ ID NO: 39: aaaaaa;

SEQ ID NO: 27: tttttt.
```

In certain embodiments of all aspects and other embodiments of the current invention, a pair of two separate compatible binding partners is employed in the method according to the invention. In certain embodiments, the pair is a pair of all-LNA single-stranded-oligonucleotides whereof one is used as nucleic acid tag in the alcohol residue of the artificial substrate according to the invention and the other is used to capture/immobilize the free alcohol residue in the method according to the invention. In certain embodiments, the pair of all-LNA single-stranded-oligonucleotides is selected from the group consisting of

```
(SEQ ID NO: 01) : (SEQ ID NO: 02);

(SEQ ID NO: 09) : (SEQ ID NO: 10);

(SEQ ID NO: 11) : (SEQ ID NO: 12);

(SEQ ID NO: 13) : (SEQ ID NO: 14);

(SEQ ID NO: 09) : (SEQ ID NO: 15);

(SEQ ID NO: 16) : (SEQ ID NO: 20);

(SEQ ID NO: 21) : (SEQ ID NO: 18);
```

-continued

```
(SEQ ID NO: 21) : (SEQ ID NO: 20);

(SEQ ID NO: 21) : (SEQ ID NO: 19);

(SEQ ID NO: 23) : (SEQ ID NO: 17); and

(SEQ ID NO: 25) : (SEQ ID NO: 28)
```

In one preferred embodiment of all aspects and other embodiments of the invention, the pair of two separate compatible binding partners is the pair of all-LNA single-stranded-oligonucleotides of SEQ ID NO: 16 and SEQ ID NO: 20. Thus, the binding pair is gttggt: accaac.

DESCRIPTION OF SPECIFIC EMBODIMENTS OF THE INVENTION

Herein is reported a new assay using a tri-partite artificial hydrolase substrate that mimics polysorbate. If a hydrolase, such as, e.g., an esterase or lipase, is present in a sample to be analyzed, the artificial hydrolase substrate is cleaved by the hydrolase and the production of enzymatic cleavage products, i.e. of the free alcohol residue of the artificial substrate, is detected.

The detection of the released alcohol residue of the artificial hydrolase substrate in the method according to the invention is by a label attached thereto. The label can be freely chosen. Therefore, the detection can be by any known method, such as, e.g., Simoa®, Gyrolab®, Elecsys®, ELISA, etc.

In one preferred embodiment, the hydrolase is an esterase and the detection is with an electrochemiluminescense immunoassay.

The invention is based, at least in part, on the finding that the presence of high monomeric bovine serum albumin is advantageous with respect to assay sensitivity. Thereby the hydrolytic enzymatic activity of hydrolases could be increased. Concomitantly the sensitivity of the assay could be increased. Thereby a detection limit in the low one digit picomolar range (1 pg/mL) and a quantification limit in the low two-digit picomolar range (10 pg/mL) could be established.

In the following, an exemplary description of the method according to the current invention is presented. This is done solely to outline the method according to the current invention. It shall not be construed as limitation. The true scope of the invention is set forth in the appended claims.

For the production of pharmaceuticals, CHO cells are preferred. During the manufacturing process, i.e. the cultivation, a cell lysis occurs. Thereby, inter alia, proteases and hydrolases are released. As the therapeutic proteins are secreted into the extracellular medium, they come in contact with the released host cell protein (HCP) impurities. Some HCPs have physicochemical properties similar to those of the pharmaceuticals and are consequently co-purified. Other HCPs are co-purified as hitchhikers together with the pharmaceutical due to direct protein-protein-interactions [1].

In the downstream process (DSP) the HCP contamination must be reduced to an acceptable level, because even small amounts of HCP contamination can have an impact on the product quality and stability or/and trigger negative effects in the patient, such as immune reactions. This is achieved by using purification steps. However, some HCPs are difficult to remove in the DSP because they participate in non-covalent interactions with the product and have a chromatographic behavior similar to that of the therapeutic protein [2].

More than 90% of the HCPs are usually be removed by protein A chromatography in the DSP [3]. Further purification (polishing) steps, such as hydrophobic interaction chromatography (HIC), help to significantly reduce the residual HCP concentrations [4]. However, trace amounts of HCPs remain in the preparation. This is taken into account by the health authorities by stipulating that the presence of HCPs is minimized to an acceptable residual amount, i.e. below a defined threshold value for each product [5]. Most of the biotechnological products approved by the Food and Drug Administration (FDA) have HCP contaminants below 100 ppm.

HCP contaminants are usually detected using quantitative immunological tests such as ELISA. However, a multi-analyte ELISA only detects the total amount of HCPs, and identity or amount of the individual HCPs present cannot be deduced thereby. Liquid chromatography coupled with tandem mass spectrometry (LC-MS/MS) and protein-specific ELISAs are suitable for identifying individual HCPs. Since the amounts of HCPs in relation to the active pharmaceutical ingredient (API) are usually very small, identification and quantification with using LC-MS/MS is even hampered after enriching those HCPs [6].

Protein aggregation in biotherapeutics is associated with immune reactions and the loss of the active pharmaceutical ingredient. A common method to reduce non-specific interactions and to stabilize the protein is to add surface-active compounds to protein formulations.

What are termed surfactants or detergents consist of molecules, which have a polar hydrophilic and a non-polar hydrophobic part; these are referred to as amphiphiles. They reduce interfacial stresses and increase the solubility of the product [11].

Surfactants can be subdivided into four main groups: Anionic, cationic, zwitterionic, and non-ionic surfactants. Anionic surfactants have a negative charge on the polar part of the molecule, whereas cationic surfactants have a positive charge on the polar end. Zwitterionic surfactants have positive and negative charges that depend on the environment, and non-ionic surfactants have no charge on their hydrophilic part of the molecule.

Polysorbates are non-ionic surfactants that are widely used in the pharmaceutical industry due to their stabilizing properties, low toxicity, and high biocompatibility [12]. The most frequently used surfactants for pharmaceutical products are polysorbate 20 (PS20), polysorbate 80 (PS80), and poloxamer 188, which are usually added to the product in mass concentrations between 0.001% and 0.1% [13].

Polysorbates belong to the group of poly(ethylene glycol) sorbitan fatty acid esters. They are composed of 20 ethylene oxide units, a sorbitan ring, and a fatty acid consisting of 12-18 carbon atoms. The fatty acid ester in PS20 is mainly formed with lauric acid, and is thus referred to as polyoxyethylene (POE)-(20)-sorbitan monolaurate. PS80 contains predominantly oleic acid, and is thus referred to as polyoxyethylene-(80)-sorbitan monooleate [14-21]. FIG. 1 shows an idealized polysorbate structure.

As is well known industrial polysorbates are mainly heterogeneous mixtures with different attached fatty acids and a varying degree of esterification (see Table 1).

TABLE 1

Percentage composition of the containing fatty acids in the heterogeneous mixtures of polysorbate 20 and 80 according to the European Pharmacopoeia (Ph. Eur.) and United States Pharmacopoeia (USP). The fatty acids in bold type are the most common fatty acids for the respective polysorbate

| Polysorbate 20 | | Polysorbate 80 | |
|---|---|---|---|
| caproic acid | ≤1.0% | myristic acid | ≥5.0% |
| caprylic acid | ≤10.0% | palmitic acid | ≥16.0% |
| capric acid | ≤10.0% | palmitoleic acid | ≥8.0% |
| **lauric acid** | **40.0-60.0%** | stearic acid | ≥6.0% |
| myristic acid | 14.0-25.0% | **oleic acid** | **≥58.0%** |
| palmitic acid | 7.0-15.0% | linoleic acid | ≥18.0% |
| stearic acid | ≤7.0% | linolenic acid | ≥4.0% |
| oleic acid | ≤11.0% | | |
| linoleic acid | ≤3.0% | | |

An advantage of polysorbates is that they are readily biodegradable [22]. However, this advantage is also their greatest disadvantage in terms of stability in protein formulations. This has been a major challenge in the pharmaceutical industry for several years. In some cases, polysorbates undergo considerable degradation that could lead to the therapeutic proteins no longer being adequately protected from interface interactions [23].

Moreover, in case the free fatty acids accumulate, they can excess their limit of solubility and precipitate out and form visible particles that can affect the product stability and quality [24]. Due to the complex interrelationship between surfactant, active ingredient, and free fatty acids, the underlying mechanism of action that promotes precipitation via a specific nucleation event is not yet fully understood, and can vary from formulation to formulation [25]. Particles in parenteral products are undesirable because they could harm patients [23, 26].

Super refined and high purity grade are two types of PS20 that are used in the formulation of biopharmaceuticals. Compared to high purity grade PS20, super refined PS20 contains a higher proportion of di- and higher-order esters, which play a crucial role in solubilizing free fatty acids. In addition, super refined PS20 is characterized by a lower level of process-related impurities, such as free fatty acids, therefore reducing or deferring the occurrence of particle formation [27].

Polysorbate degradation can either take place by oxidation or by hydrolysis (see FIG. 2) [28].

Hydrolysis of fatty acid esters can take place either enzymatically or via an acid/base catalyzed mechanism. The latter is negligible under normal storage and formulation conditions, as the acid/base-catalyzed mechanism has mainly been found to play an important role in experiments carried out at high pH and elevated temperatures [29].

The enzymatic degradation of polysorbate is not well characterized than the chemical degradation, and only a few of the responsible enzymes have been identified [30, 31, 73]. Hall, et al., identified the lysosomal phospholipase A2 (LPLA2) in purified antibodies that led to polysorbate degradation, while antibodies in the absence of LPLA2 showed no polysorbate degradation [30]. Dixit, et al., found that phospholipase B-like 2 (PLBL2) is involved in polysorbate degradation [32]. In this study, however, a recombinant variant having a purity of about 90% for this protein was used. Possible enzymatic contamination can therefore not be completely ruled out. The study by Zhang, et al., examined the purity of the recombinant PLBL2, and they were able to identify several different lipases. Thus, the increase in hydrolysis activity in Dixit, et al., can be possibly attributed to a contamination with lipases. In addition, Zhang, et al., showed that the PLBL2-depleted samples did not lead to a reduction in lipase activity. Likewise, no correlation could be established between the concentration of PLBL2 in the sample and the polysorbate degradation [33]. The study by Chiu, et al., showed that the removal of lipoprotein lipase (LPL) using LPL knockout CHO cells helps to reduce the breakdown of PS20 and PS80 [31].

The hydrolytic degradation leads to the release of free fatty acids and non-esterified sorbitan/isosorbide forms. The solubility of the fatty acids decreases with increasing chain length. This can promote particle formation [34, 35, 36]. A risk factor for the product quality of pharmaceutical solutions is the appearance of fatty acid particles that can be either visible or invisible to the human eye, originating from the cleavage of the polysorbate [37, 38]. The observed fatty acid particles can be clearly differentiated from protein particles using analytical methods. The fatty acid particles are largely composed of the cleaved long-chain free fatty acids, which are poorly soluble in aqueous solutions, especially at low temperatures [24].

There are various methods of analyzing polysorbate breakdown. One method is to measure the hydrolytic enzymatic activity of in-process samples. Another is to carry out determinations of the free fatty acids. A further method is mixed-mode liquid chromatography with a light scattering detector (HPLC-ELSD) to determine the remaining PS20 content [17]. Still, another possibility is the fluorescence micelle assay, in which the fluorescent dye N-phenyl-1-naphthylamine is absorbed into the hydrophobic core of the PS micelle to enable determination of the polysorbate content [39].

The Lipase Enzymatic Activity for Polysorbates (LEAP) assay can be used to determine the hydrolase/hydrolase activity, i.e. the hydrolytic activity, of in-process samples [40]. As shown graphically in FIG. 3, hydrolytically active components present in the sample cleave the ester bond of the non-fluorescent substrate, the 4-methylumbelliferyl fatty acid ester. This leads to an increase in the fluorescent alcohol residue, the 4-methylumbelliferone (MU). The increase in the fluorescence signal, with an extinction of 355 nm and an emission of 460 nm, is continuously monitored while the assay is incubated in a plate reader at 37° C. for two hours.

The MU production rate is derived from the slope of the fluorescence time curve and represents the initial rate of a reaction ($k_{raw}$). This method requires an enzyme blank value reaction that represents the self-cleavage rate of the substrate in a certain sample matrix ($k_{self\ cleavage}$). The lipase activity of a sample is determined according to equation (1) by subtracting the rate of self-cleavage from the initial rate and converting the fluorescence signal to μμM MU by running a standard curve for MU on the same plate.

$$\text{Lipase Activity} = \frac{k_{raw} - k_{self\ cleavage}}{a}, \tag{1}$$

$k_{raw}$=reaction rate of the sample in RFU/h, $k_{self\ cleavage}$=reaction rate of the enzyme blank value in RFU/h, a=calculated conversion factor of the fluorescence signal into the concentration of MU in RFU/μM.

The limit of quantification (LOQ) of this assay is 0.1 μM MU/h and the limit of detection is 0.4 μM MU/h [40].

The Free fatty Acid Mass Spectrometry (FAMS) method for quantifying FFAs (free fatty acids) [41] is carried out using ultra-high liquid chromatography, e.g., coupled to a mass spectrometer (UPLC-MS). The separation of the molecules for FFA analysis is based on reverse phase liquid chromatography (RPLC). Among all RPLC columns, the octadecyl (C18) column is the most common. Hydrophobic molecules have a high affinity for the stationary phase, while hydrophilic molecules have a lower affinity for the column, so they pass through it faster and are detected first. Therefore, the shorter lauric acid with a C12 chain is eluted first, followed later by the longer myristic acid with a C14 chain [42].

Mass spectrometry is used as an analytical technique to determine the mass of molecules. An ion source, in this case electron spray ionization (ESI), generates gas ions from the molecules in the liquid phase. The mass analyzer separates the ions according to their mass-to-charge ratio (m/z) and the detector, the QDa, counts the ions for each m/z ratio [43].

The concentration of free fatty acids is calculated according to equation (2) as follows:

$$FFA \text{ concentration} = \frac{\sum FFA \text{ area}}{\sum IS \text{ area}} \times \text{Dilution factor} \times IS \text{ concentration} \tag{2}$$

TABLE 2

The LOQ and the working ranges of the FAMS method.

| FFA | Working range (μg/mL) | LOQ (μg/mL) |
|---|---|---|
| Lauric acid | 0.05-40 | 0.0497 |
| Myristic acid | 0.05-40 | 0.0497 |
| Palmitic acid | 0.2-40 | 0.1757 |
| Stearic acid | 0.2-40 | 0.1153 |

Small amounts of enzymes are responsible for the cleavage of the polysorbate in pharmaceutical products, which are difficult or impossible to detect using existing analytical methods such as LEAP or FAMS.

Both LEAP and FAMS have limiting factors. The LEAP assay is a robust but not very sensitive assay. Residual hydrolase/hydrolase activity, i.e. hydrolytic activity, cannot be detected at low level, e.g. in the final process steps. FAMS is a very robust and sensitive method, but it is very time-consuming to use. Other methods require sample preprocessing or chromatographic pre-separation prior to performing the determination of the hydrolase/hydrolase activity (hydrolytic activity).

As described herein, previously used methods for both the identification/quantification of HCPs and the determination of hydrolytic activity are hampered by the miniscule amounts of HCPs responsible for polysorbate degradation in biopharmaceutical formulations.

For these reasons, a suitable method is required for a quick, sensitive, and specific detection of hydrolase/hydrolase activity (hydrolytic activity), i.e. of hydrolytically active HCPs.

The current invention is based, at least in part, on the finding that in certain embodiments an Electroluminescence-based immunoassay based Polysorbase Assay (EPA) can overcome at least all these limiting factors as outlined before.

The EPA according to the current invention based on the hydrolysis of a tri-partite artificial esterase substrate. For detection, an electrochemiluminescense immunoassay-based (ECLIA) method can be used. ECLIA is an analytical, highly selective and sensitive technique that can be used to determine the enzymatic activity using an appropriate (artificial) substrate.

The method according to the current invention delivers results for enzymatic activity determinations faster and more sensitive than the assays mentioned above.

The detection of the polysorbate degradation caused by the hydrolase/hydrolase activity (hydrolytic activity) of the HCPs (still) present in a sample is achieved by combining hydrolytic cleavage with an immunoassay-based quantification of the resulting enzymatic cleavage product.

An artificial substrate that is supposed to imitate polysorbate was used for this. In FIG. 4, a functional sketch of the artificial substrate is presented. The essential feature of the substrate is that different functional groups are attached to the carboxylic acid residue and the alcohol residue, respectively.

In more detail, due to the low catalytic activity it is beneficial for the determination of hydrolase/hydrolase activity (hydrolytic activity) to remove one of the cleavage products as well as not-cleaved artificial substrate from the reaction mixture.

Therefore, one of the residues of the artificial substrate is conjugated to a first label. The kind of conjugation and type of the first label is not limited as long as the conjugation is stable under the assay conditions and the first label can specifically be bound by a binding partner in the presence of a nucleic acid tag and a second label. The first label is used to bind the respective conjugated residue and intact artificial substrate, respectively, to a solid phase immobilizing these compounds. This allows for an easy removal thereof. The respective other residue remains in solution and can be separated from the solid phase by standard techniques. In one preferred embodiment, the carboxylic acid residue of the artificial substrate is conjugated to the first label.

For detection, the respective other residue is conjugated to a second label. This residue is the detected/quantified cleavage product. The second label is different from the first label so that both labels can be selectively bound in the presence of each other. Besides that, no further requirements have to be placed on the second label. In one preferred embodiment, the detected/quantified cleavage product is the alcohol residue of the artificial substrate.

For improving the determination and quantification of the residue conjugated to the second label, an immobilization tag can further be conjugated to the detected/quantified residue. Thereby the detection/quantification can be performed as solid phase reaction, e.g. in an ELISA or ECLIA. In one preferred embodiment, the immobilization tag is a nucleic acid tag.

Beside the above outlined functional features, no limitations with respect to the structure of the artificial substrate are required. Thus, a person skilled in the art can design artificial substrates suitable for performing the method according to the current invention easily without undue burden based on his technical knowledge employing scaffolds, linkers, labels, conjugation methods and immobilization tags well known to him/her.

Hydrolytically active HCPs cleave the ester bond and release an alcohol residue and a carboxylic acid residue from the artificial substrate (see FIG. 4). The R1 on the carboxylic acid residue as well as the R1 on the non-cleaved artificial substrate enters into a non-covalent biological bond with its binding partner and is then removed. The remaining alcohol, which contains R2 and R3, can be determined by a specific antibody binding to R3, which is labelled, e.g. with ruthenium complexes for electrochemiluminescense-based detection. A class of high-affinity RNA analogues (R2), e.g. LNA, are used for capturing the alcohol residue on magnetic beads that are coated with nucleic acids having complementary sequences.

For example, in case an antibody labelled with ruthenium complexes is used for electrochemiluminescense-based detection, the incubation/reaction mixture is transferred into the measuring cell of a Cobas e411 system (Roche Diagnostics GmbH, Mannheim, Germany) and the magnetic microparticles are held on the electrode surface. Everything that is not adhered to the electrode surface is removed by a washing step. A voltage is applied to the electrode to induce the chemiluminescence emission, which is measured with a photomultiplier. The results are then determined using an external calibration curve.

The invention is based, at least in part, on the finding that of the possible influencing factors, such as, e.g., buffer salt type, bivalent salt, temperature, as well as the concentrations of buffer, presence of NaCl, methionine, concentration and type of BSA, in the pH range of from pH 7 to pH 8 the factors type and concentration of BSA, presence of NaCl, and the interaction of BSA*NaCl have a statistically significant influence on the enzyme activity (see FIG. 5 and Example 1). The non-significant factors are shown in a half-normal probability plot on a line with normal distribution. The significant factors deviate from this line. The further a factor is from the line, the greater its influence.

The invention is based, at least in part, on the finding that of the possible influencing factors such as, e.g., buffer salt type, bivalent salt, temperature, as well as the concentrations of buffer, NaCl, methionine, BSA, and the bivalent salts at an acidic pH value within the range between pH 6-7, the factors concentration of the buffer, BSA, and additionally the interaction of BSA*NaCl have a statistically significant influence on the enzyme activity (see FIG. 6 and Example 1).

The invention is based, at least in part, on the finding that the addition of intermediate concentrations of a detergent has a positive effect on the enzyme activity. This is especially the case when the sample comprises only minute amounts of hydrolase/hydrolase activity (hydrolytic activity).

The effect of the presence or absence as well as the concentration of the detergent is shown in FIG. 7. As exemplary sample, a purified monoclonal antibody preparation has been used. This sample has already been purified using two chromatography steps and thus comprises only minute amounts of residual hydrolase/hydrolase activity (hydrolytic activity). As exemplary detergent Triton® X-100 has been used. It can be seen that in the absence of detergent the onset of the cleavage of the artificial substrate is delayed. In contrast thereto, in the presence of 0.25% (w/v) detergent the enzymatic reaction becomes suppressed. At an intermediate concentration, neither delay of the reaction nor suppression of the reaction is seen. Thus, in one preferred embodiment, the concentration of the detergent is in a range of and including 0.05% (w/v) to 0.15% (w/v).

In certain embodiments of all aspects and other embodiments of the invention, the buffered solution or the incubation mixture further comprises a detergent.

In certain embodiments, the detergent is a non-ionic detergent.

In certain embodiments, the detergent is an aromatic hydrocarbon lipophilic or hydrophobic group with hydrophilic polyethylene oxide chains. In certain embodiments, the detergent has on average it has 9.5 ethylene oxide units and the hydrocarbon is a 4-(1,1,3,3-tetramethylbutyl)-phenyl group. In certain embodiments, the detergent is octoxinol-9. Octoxinol-9 is marketed under the tradenames Triton X-100 and Nonidet P40.

In certain embodiments, the detergent is an alkyl polyglucoside. In certain embodiments, the detergent is a mixture of 58.0-62.0 (w/v) % D-glucopyranose, oligomeric, decyl octyl glycoside and 38.0-42.0 (w/v) % water.

The effect of temperature on the assay according to the invention is shown in FIG. 8. As sample a protein A chromatography purified monoclonal monospecific antibody has been used. The sample was processed in the method according to the current invention at different temperatures of 34° C., 37° C. and 40° C. for 22 hrs. The blank corrected values are plotted in FIG. 8 as bar diagram.

The invention is based, at least in part, on the finding that the use of (3-(N-morpholino)propane sulfonic acid) (MOPS) as buffer in the method according to the invention results in a better assay sensitivity.

As an example, a MOPS-based buffer has been compared with a TRIS-based buffer. The composition of the 10× stock solutions is shown in the following Table 3.

TABLE 3

Buffer compositions.

| TRIS-based buffer (10x) | | MOPS-based buffer (10x) | |
|---|---|---|---|
| Tris-Cl | 3.0M | MOPS | 1.5M |
| $MgCl_2$ | 50 mM | $MgCl_2$ | 50 mM |
| BSA | 60 μM | BSA | 60 μM |
| NaCl | 250 mM | NaCl | 250 mM |
| Triton X-100 | 1% | Triton X-100 | 1% |
| pH @ 37° C. | 7 | pH @ 37° C. | 7 |

The concentration, which could be used for the preparation of the buffer, depends on the solubility of the respective buffer salt in water. Thus, for preparing a 10× concentrated stock solution a concentration of 1.5 M MOPS was used. Likewise, a concentration of 3 M TRIS was used. Both being close to the solubility of the respective buffering agent in water at a pH value of 7. This shall provide for the highest buffering capacity in both cases.

The amount of generated hydrolysate was determined. The results are shown in the following Table 4 and FIG. 12 as bar graph (TRIS-based buffer on the left, MOPS-based buffer on the right).

TABLE 4

Amount of hydrolysate generated depending on the used buffer.

| assay incubation | amount hydrolysate generated [pg/mL] | |
|---|---|---|
| time [h] | TRIS-based buffer | MOPS-based buffer |
| 0 (blank) | 52 | 27 |
| 1 | 188 | 170 |
| 3 | 312 | 536 |
| 5 | 416 | 888 |
| 7 | 569 | 1133 |
| 22 | 1063 | 2449 |

It can be seen that the use of a MOPS-based buffer results in increased hydrolase/hydrolase activity (hydrolytic activity). Without being bound by this theory it is assume that the pKa value of MOPS of 7.02 at 37° C. is resulting in better buffering capacity at a pH value of 7.0.

The invention is based, at least in part, on the finding that BSA has a significant influence on enzyme activity. Especially, the invention is based, at least in part, on the finding that the use of an inert bovine serum albumin results in an increased signal-to-noise ratio and thereby an improved sensitivity.

The presence of BSA in the buffer leads to an improvement in the enzyme activity, and, thus, also increases the sensitivity of the assay.

BSA from different sources, i.e. vendors, have been compared as shown in the following Table 5.

TABLE 5

Different BSA sources.

| | |
|---|---|
| 1 | Cys 34 oxidized BSA; Roche (average of 5 experiments) |
| 2 | Proliant Biologics; BSA, reagent grade; Cat. No. 68700, Lot BB31080101 |
| 3 | Sigma-Aldrich; lyophilized powder, essentially fatty acid free, ≥96%; Cat. No. A6003, lot# SLCC7677 |
| 4 | no BSA added |

The relative results, i.e. blank corrected and normalized to the minimal overall value, are shown in the following Table 6 and FIG. 13.

TABLE 6

Relative amount of hydrolysate generated depending on the used BSA.

| | incubation time | | | | | |
|---|---|---|---|---|---|---|
| BSA | 0 h | 1 h | 3 h | 5 h | 7 h | 22 h |
| 1 | 190% | 227% | 683% | 1361% | 1724% | 3897% |
| 2 | 112% | 196% | 681% | 552% | 882% | 3065% |
| 3 | * | * | 426% | 822% | 1466% | 3233% |
| 4 | * | 100% | 593% | 541% | 1264% | 2467% |

*negative value after blank correction

It can be seen that the use of a Cys 34 oxidized BSA results in the best hydrolase/hydrolase activity (hydrolytic activity). Without being bound by this theory, it is assumed that by using the inert bovine serum albumin the hydrolytic enzymatic activity in the sample could be increased and thereby the sensitivity of the assay was increased. In one preferred embodiment, the inert bovine serum albumin is a bovine serum albumin with more than 80% of the cysteine residue at position 34 being oxidized/in oxidized form. In certain embodiments, more than 90% of the cysteine residue at position 34 is oxidized/in oxidized form. In certain embodiments, 95% or more of the cysteine residues at position 34 is oxidized/in oxidized form. In one preferred embodiment, more than 80% of the bovine serum albumin is present in monomeric form (not conjugated to a second polypeptide at cysteine residue 34). In certain embodiments, more than 90% of the bovine serum albumin is present in monomeric form. In certain embodiments, 95% or more of the bovine serum albumin is present in monomeric form.

The scheme of an exemplary assay according to the invention is shown FIG. 9.

In one preferred embodiment of all aspects and other embodiments of the invention, the incubation mixture of the assay according to the invention comprises 20-30 mM sodium chloride, 3-10 μM BSA with a monomeric content of 95% or more/with oxidized Cys34, 100-200 mM MOPS, 3-10 mM magnesium chloride, 0.05-0.15% (w/v) detergent, the therapeutic polypeptide has a concentration of 0.1-250 mg/mL, has at pH value of 6.8 to 7.2, and the incubation is performed at 35-40° C. for 8 to 36 hours.

In certain embodiments of all aspects and other embodiments of the invention, steps a) and b) are performed in parallel with two different aliquots of the sample and the aliquots are combined prior to performing step c).

In the following comparative data of the assay according to the invention and the FAMS assay is presented.

The readout of the assay according to the invention is a rate with a unit of pg/mL/mg/h whereas the readout of the FAMS assay is a rate with a unit of ng/mg/d. Thus, the results of these two assays are not directly comparable. As outlined above the regulatory authorities require the reduction of HCPs below a certain threshold limit. Likewise, the reduction of hydrolase/hydrolase activity (hydrolytic activity) has to be done under a threshold limit so that particle formation is prevented. Therefore, the comparison of the assays has been done using relative rates, i.e. the determination of relative residual hydrolase/hydrolase activity (hydrolytic activity) in the tested samples compared to a starting value.

Samples comprising different therapeutic polypeptides and at different stages of purification have been analyzed. As these therapeutic polypeptides are different also different sequence of chromatography steps have been used for the respective purification. As the assay according to the current invention is for the determination of residual hydrolase/hydrolase activity (hydrolytic activity) this difference has no impact on the assay readout as aliquots of the same samples have been used for both assays. Likewise, the specific sequence or binding specificity of the therapeutic polypeptides does not influence the assay.

Therapeutic polypeptide 1 is a full-length bivalent, bispecific antibody of the IgG1 subclass in CrossMab format.

Therapeutic polypeptide 2 is a full-length bivalent, monospecific antibody of the IgG1 subclass.

Therapeutic polypeptide 3 is a trivalent, bispecific antibody in TCB format.

Therapeutic polypeptide 4 is a full-length bivalent, monospecific antibody.

Therapeutic polypeptide 5 is a bivalent, bispecific Fab.

Below a threshold value for residual hydrolase/hydrolase activity (hydrolytic activity) in a therapeutic polypeptide preparation, no visible polysorbate degradation occurs during storage. Thus, it is needed to determine if a therapeutic polypeptide preparation has hydrolase/hydrolase activity (hydrolytic activity) below a threshold value to ensure suitable storage periods.

In order to compare the results of the assay according to the current invention and the FAMS assay the difference of the respective measurements has been used. Therefore, it is assumed that the average of the results of the two assays is the correct value.

As outlined above it is required to determine residual hydrolase/hydrolase activity (hydrolytic activity). Thus, for methods to be comparable the residual hydrolase/hydrolase activity (hydrolytic activity) determined with different methods should be within 100% of each other. This percent difference expresses as a percentage the difference between the measured value and an assumed exact value. That is, it is used to report the difference between a measured value and an exact value, i.e. to gauge how close a measured value is to a true value.

The respective data is shown in Table 7.

TABLE 7

Experimental comparative results of FAMS and EPA.

| therapeutic polypeptide | sample | method | rel. hydrolase/ hydrolase activity (hydrolytic activity) | difference |
|---|---|---|---|---|
| 1 | load chromatography 1 | FAMS | 100% | 0% |
| | | EPA-2 | 100% | |
| | load chromatography 2 | FAMS | 27% | 19% |
| | | EPA-2 | 39% | |
| | eluate chromatography 2 | FAMS | n.d. | n.c. |
| | | EPA-2 | 29% | |
| | unconditioned bulk | FAMS | 1% | 33% |
| | | EPA-2 | 2% | |
| 2 | load chromatography 1 | FAMS | 100% | 0% |
| | | EPA-2 | 100% | |
| | eluate chromatography 1 | FAMS | 15% | 6% |
| | | EPA-2 | 17% | |
| | eluate chromatography 2 | FAMS | 11% | 69% |
| | | EPA-2 | 2% | |
| | UFDF pool | FAMS | 8% | 78% |
| | | EPA-2 | 1% | |
| 3 | eluate chromatography 1 | FAMS | 100% | 0% |
| | | EPA-2 | 100% | |
| | eluate chromatography 2 | FAMS | 20% | 18% |
| | | EPA-2 | 29% | |
| | eluate chromatography 3 | FAMS | 14% | 0% |
| | | EPA-2 | 14% | |
| | unconditioned bulk | FAMS | 13% | 53% |
| | | EPA-2 | 4% | |
| 4 | eluate chromatography 1 | FAMS | 100% | 0% |
| | | EPA-1 | 100% | |
| | eluate chromatography 2 | FAMS | 36% | 1% |
| | | EPA-1 | 37% | |
| | eluate chromatography 3 | FAMS | n.d. | n.c. |
| | | EPA-1 | 18% | |
| | unconditioned bulk | FAMS | 0.2% | 100% |
| | | EPA-1 | 0% | |
| 5 | eluate chromatography 1 | FAMS | 100% | 0% |
| | | EPA-1 | 100% | |
| | eluate chromatography 2 | FAMS | 20% | n.c. |
| | | EPA-1 | n.d. | |
| | eluate chromatography 3 | FAMS | 15% | 41% |
| | | EPA-1 | 36% | |
| | unconditioned bulk | FAMS | 4% | 11% |
| | | EPA-1 | 5% | |

n.d. = not determined n.c. = not calculable due to not determined value

EPA-1 = assay according to the invention with 100 ng/mL therapeutic polypeptide in the incubation mixture; no sample pooling prior to determination; 1:3 dilution prior to electrochemiluminescense measurement EPA-2 = assay according to the invention with 200 ng/mL therapeutic polypeptide in the incubation mixture; pooling of two parallel incubated aliquots prior to determination; no further dilution prior to electrochemiluminescense measurement For therapeutic polypeptide 3 as an example the data from the Table above is presented in FIG. 10 and FIG. 11 as bar graphs. It can be seen that the assay according to the invention and the FAMS assay, which is the most sensitive assay for the determination of hydrolase/hydrolase activity (hydrolytic activity), provide comparative data, but the assay according to the current invention can be performed within 48 hours instead of two weeks as the required for the FAMS assay.

The following examples and figures are provided to aid the understanding of the present invention, the true scope of which is set forth in the appended claims. It is understood that modifications can be made in the procedures set forth without departing from the spirit of the invention.

CITED DOCUMENTS

1. Pilely, K., et al., Biotechnol. Prog. 2020: p. e2983.
2. Valente, K. N., et al., Biotechnol. Bioeng. 2015. 112(6): p. 1232-1242.
3. Shukla, A. A. and P. Hinckley, Biotechnol. Prog. 2008. 24(5): p. 1115-1121.
4. Bresolin, I. R. A. P., et al., J. Biotechnol., 324 (2020) 100020.
5. Wang, X., et al., Biotechnol. Bioeng. 2009. 103(3): p. 446-458.
6. Thompson, J. H., et al., Rapid Comm. Mass Spectrom. 2014. 28(8): p. 855-860.
7. Ransac, S., et al., The kinetics, specificities and structural features of lipases, in Molecular Dynamics of Biomembranes. 1996, Springer. p. 265-304.
8. Verger, R., Trends Biotechnol. 1997. 15(1): p. 32-38.
9. Scheib, H., Untersuchungen zur Regio-und Stereoselektivität von Lipasen durch computergestütztes Molecular Modeling und molekularbiologische Methoden. 1999.
10. Khan, F. I., et al., Front. Bioeng. Biotechnol. 2017. 5: p. 16.
11. Zhang, L., et al., Pharm Res, 2018. 35(2): p. 33.
12. Honemann, M. N., et al., J. Chrom. B Anal. Technol. Biomed. Life Sci., 2019. 1116: p. 1-8.
13. Sekhon, B. S., Surfactants: pharmaceutical and medicinal aspects. 2014.
14. Ayorinde, F. O., et al., Rapid Comm. Mass Spectrom, 2000. 14(22): p. 2116-24.
15. Brandner, J. D., Drug Devel. Ind. Pharm., 1998. 24(11): p. 1049-1054.
16. Frison-Norrie, S. and P. Sporns, J. Agric. Food Chem., 2001. 49(7): p. 3335-3340.
17. Hewitt, D., et al., J. Chrom. A, 2011. 1218(15): p. 2138-45.
18. Li, Y., et al., Anal. Chem., 2014. 86(10): p. 5150-5157.
19. Lippold, S., et al., J. Pharm. Biomed. Anal., 2017. 132: p. 24-34.
20. Vu Dang, H., et al., J. Pharm. Biomed. Anal., 2006. 40(5): p. 1155-65.
21. Zhang, R., et al., J. Chrom. Sci., 2012. 50(7): p. 598-607.
22. Review, C. C. I., J. Am. Coll. Toxicol., 1984. 3(5): p. 1-82.
23. Martos, A., et al., J. Pharm. Sci., 2017. 106(7): p. 1722-1735.
24. Doshi, N., et al., Mol. Pharm., 2015. 12(11): p. 3792-3804.
25. Keratichewanun, S., et al., Pharm. Res., 2015. 32(7): p. 2458-2473.
26. Cao, X., et al., J. Pharm. Sci., 2015. 104(2): p. 433-446.
27. Doshi, N., et al., J. Pharm. Sci., 2020.
28. Dwivedi, M., et al., Int. J. Pharm., 2018. 552(1-2): p. 422-436.
29. Labrenz, S. R., J. Pharm. Sci., 2014. 103(8): p. 2268-2277.
30. Hall, T., et al., J. Pharm. Sci., 2016. 105(5): p. 1633-1642.
31. Chiu, J., et al., Biotechnol. Bioeng. 2017. 114(5): p. 1006-1015.
32. Dixit, N., et al., J. Pharm. Sci., 2016. 105(5): p. 1657-1666.
33. Zhang, S., et al., J. Pharm. Sci., 2020. 109(9): p. 2710-2718.
34. Siska, C. C., et al., J. Pharm. Sci., 2015. 104(2): p. 447-56.
35. Cheng, Y., et al., J. Pharm. Sci., 2019. 108(9): p. 2880-2886.
36. Graf, T., et al., Eur. J. Pharm. Biopharm., 2020.
37. Saggu, M., et al., Pharm. Res., 2015. 32(9): p. 2877-2888.
38. Tomlinson, A., et al., Mol. Pharm., 2015. 12(11): p. 3805-3815.
39. Kishore, R. S., et al., J. Pharm. Sci., 2011. 100(2): p. 721-31.
40. Jahn (2020) Pharm. Res. 37: 118.
41. Honemann (2019) J. Chromatogr. B 1116: 1-8; Cheng (2019) J. Pharm. Sci. 108: 2880-2886.
42. Horvath, C. and W. Melander, J. Chrom. Sci., 1977. 15(9): p. 393-404.
43. Hoffman, V. S., (ed.), Mass spectrometry: principles and applications. Vol. 1(2). 2007, Bruxellas Belgica: West Sussex: John Wiley & Sons.
44. Dahotre, S., et al., J. Pharm. Biomed. Anal., 2018. 157: p. 201-207.

DESCRIPTION OF THE FIGURES

Figure 1:
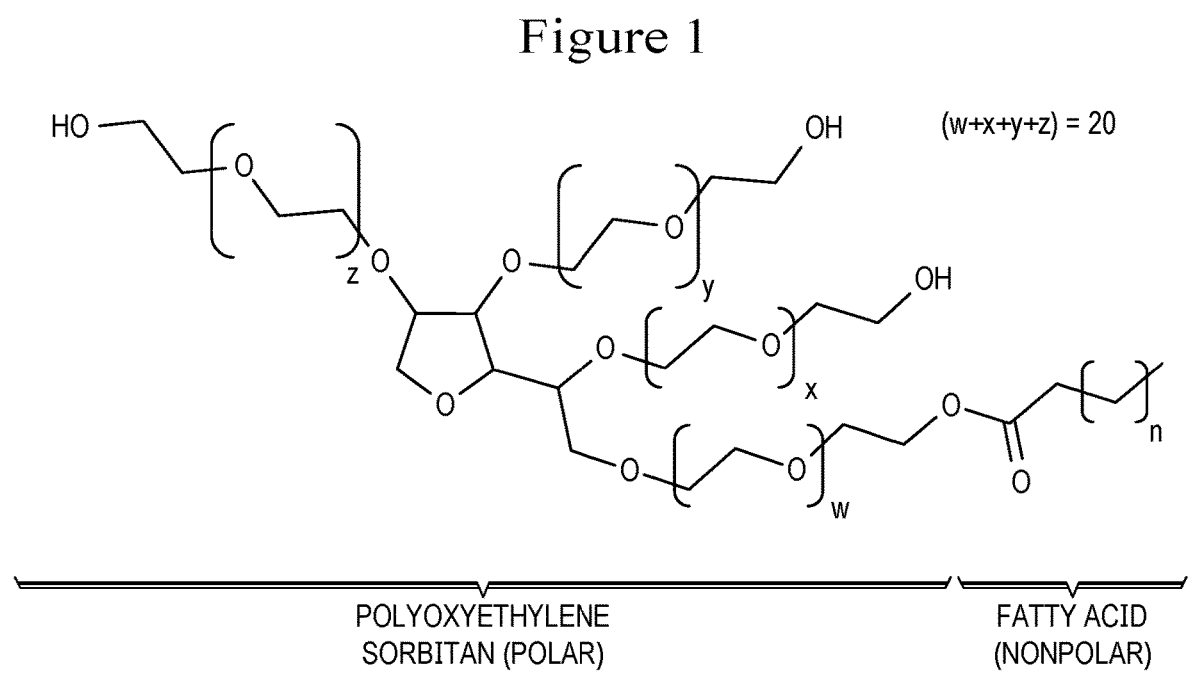

FIG. 1 Idealized polysorbate structure with non-polar fatty acids at one end and polar sorbitol and its anhydrides at the other end. Here, w+x+y+z indicates the total number of moles of ethylene oxide per mole of sorbitol and ethoxylated sorbitol anhydride, and the sum must not exceed 20.

Figure 3:
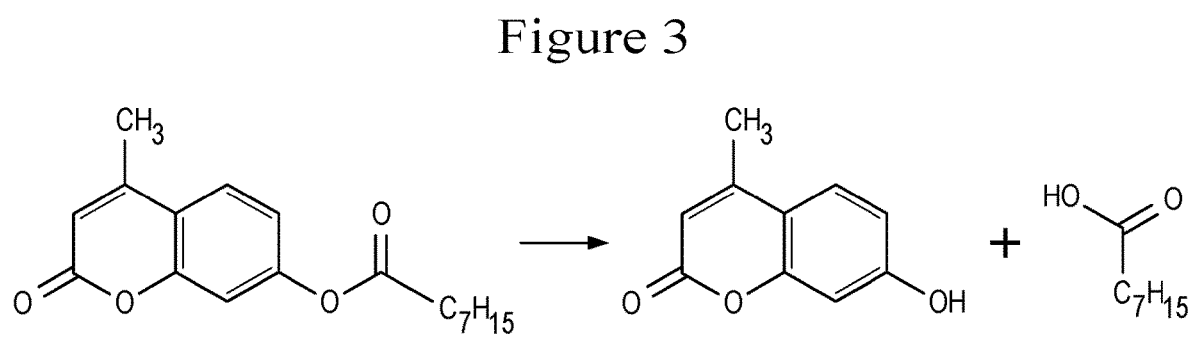

FIG. 3 Ester cleavage of the 4-methylumbelliferyl fatty acid ester into the fluorophoric head group 4-methylumbelliferone and a fatty acid.

DESCRIPTION OF THE EXAMPLES

Example 1

Design of Experiments Using Plackett-Burman Design

Figure 2:
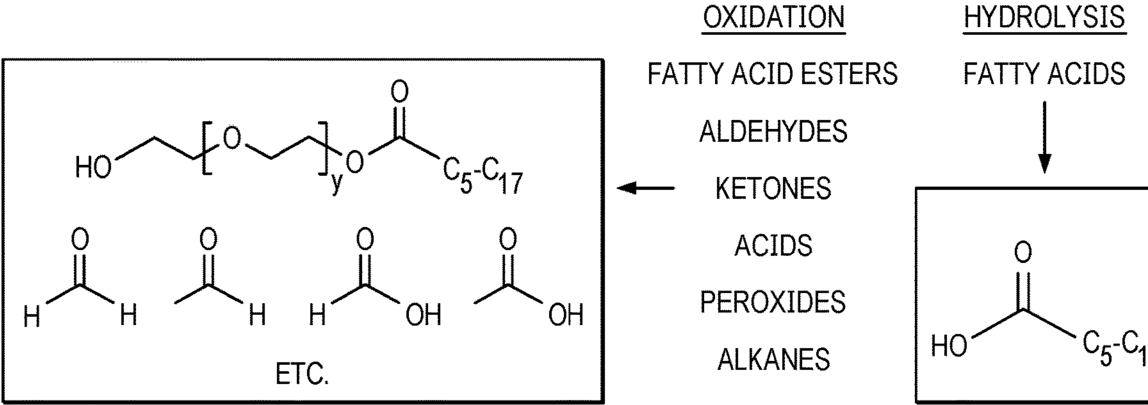
FIG. 2 Oxidative and hydrolytic degradation pathways of polysorbate 20 [44]. Long-chain fatty acids are released through hydrolytic cleavage of the fatty acid ester bond (red bolt icon). Oxidative cleavage (blue bolt icons) leads to a mixture of degradation products.

In the buffer screening process factors that have an impact on the enzyme activity have been identified.

For this experiment, a host cell culture fluid (HCCF) was used.

Two categorical factors, i.e. the buffer salts and the type of bivalent cation, as well as seven continuous factors—pH, temperature, concentrations of buffer, NaCl, methionine, BSA and the concentration of the bivalent salts were used. The conditions are summarized in Table 8 below.

TABLE 8

Conditions of the DoE; E = acid conditions; F = basic conditions.

| | | Codierte Level | |
|---|---|---|---|
| Faktor | Symbol | − | + |
| Temperatur (° C.) | A | 25 | 37 |
| Konzentration Puffer (mM) | B | 20 | 50 |
| Puffer⁺ | C | Citrat | His-Acetat |
| Puffer⁻ | D | Tris-HCl | HEPES |
| pH-Wert⁺ | E | 5 | 6 |
| pH-Wert⁻ | F | 7 | 8 |
| NaCl (mM) | G | 25 | 1000 |
| Methionin (mM) | H | 0 | 7 |
| BSA (mM) | I | 0 | 0.1 |
| Bivalente Salze | J | $CaCl_2$ | $MgCl_2$ |
| Konz. bivalente Salze (mM) | K | 5 | 10 |

For the selection of the experimental conditions, a Plackett-Burman Design was used. This design is a two-level partial factorial design in which all factors have only two values. The low (−) and high (+) values of these factors to be tested are listed in Table 8 above.

Based on these factors, two plans for the Plackett-Burman design were created (see Table 9 below). One plan served as an acidic buffer template and the other as an alkaline buffer template.

To be able to exclude chemical cleavage of the substrate by the buffer compositions, a sample in the absence of hydrolytic enzyme was also measured, a so-called buffer blank. This value was then subtracted from the respective sample value in order to give only the value of the enzyme activity

TABLE 9

Plans for the Plackett-Burman design.

| Run | A | E/F | B | C/D | G | H | I | J | K |
|---|---|---|---|---|---|---|---|---|---|
| 1 | + | − | + | − | + | − | − | − | − |
| 2 | + | − | − | − | − | + | + | − | − |
| 3 | − | + | − | + | − | − | − | − | + |
| 4 | − | + | − | − | − | − | + | + | − |
| 5 | − | − | + | + | − | − | + | − | − |
| 6 | − | − | − | + | + | − | − | + | − |
| 7 | − | − | − | − | + | + | − | − | + |
| 8 | + | + | − | + | − | + | − | − | − |
| 9 | + | − | + | − | − | − | − | + | + |
| 10 | − | + | + | − | − | + | − | − | + |
| 11 | + | + | + | − | + | − | + | − | − |
| 12 | + | + | − | − | + | − | − | + | + |
| 13 | + | − | − | + | − | − | + | + | + |
| 14 | − | + | − | − | + | + | + | + | − |
| 15 | − | − | + | + | + | + | − | + | − |
| 16 | − | − | + | − | − | + | + | + | + |
| 17 | + | + | + | + | − | + | − | + | − |
| 18 | + | − | − | + | + | + | + | − | + |
| 19 | − | + | + | + | + | − | + | − | + |
| 20 | + | + | + | + | + | + | + | + | + |

Each pattern was created as a duplicate on a 96-well plate. The Experiment was repeated twice under the same conditions.

The results for the alkaline conditions are presented in Table 10 and that for the acidic conditions in Table 11.

TABLE 10

Alkaline DoE results.

| Run | Pattern | #1 (pg/mL) | #2 (pg/mL) | Mittelwert (pg/mL) | CV (%) | Relative Enzymaktivität (%) |
|---|---|---|---|---|---|---|
| | Kontrolle (25° C.) | 593 | 593 | 593 | 0 | 100 |
| | Kontrolle (37° C.) | 619 | 499 | 559 | 0.15 | 100 |
| 1 | + − + − + − − − − | 261 | 23 | 142 | 1.19 | 25 |
| 2 | + − − − − + + − − | 5339 | 8529 | 6934 | 0.33 | 1240 |
| 3 | − + − + − − − − + | 803 | 118 | 461 | 1.05 | 78 |
| 4 | − + − − − − + + − | 9562 | 7799 | 8681 | 0.14 | 1464 |
| 5 | − − + + − − + − − | 7851 | 6163 | 7007 | 0.17 | 1182 |
| 6 | − − − + + − − + − | 116 | 47 | 82 | 0.60 | 14 |
| 7 | − − − − + + − − + | 41 | 37 | 39 | 0.07 | 7 |
| 8 | + + − + − + − − − | 2225 | 1790 | 2008 | 0.15 | 359 |
| 9 | + − + − − − − + + | −175 | −172 | −174 | −0.01 | −31 |
| 10 | − + + − − + − − + | 80 | 122 | 101 | 0.29 | 17 |
| 11 | + + + − + − + − − | 1319 | 4179 | 2749 | 0.74 | 492 |
| 12 | + + − − + − − + + | −369 | −59 | −214 | −1.02 | −38 |
| 13 | + − − + − − + + + | 5086 | 8708 | 6897 | 0.37 | 1234 |
| 14 | − + − − + + + + − | 3745 | 2978 | 3362 | 0.16 | 567 |
| 15 | − − + + + + − + − | 135 | 23 | 79 | 1.00 | 13 |
| 16 | − − + − − + + + + | 7361 | 6155 | 6758 | 0.13 | 1140 |

TABLE 10-continued

Alkaline DoE results.

| Run | Pattern | #1 (pg/mL) | #2 (pg/mL) | Mittelwert (pg/mL) | CV (%) | Relative Enzymaktivität (%) |
|---|---|---|---|---|---|---|
| 17 | + + + + − + − + − | −19 | −122 | −71 | −1.03 | −13 |
| 18 | + − − + + + + − + | 1654 | 3807 | 2731 | 0.56 | 488 |
| 19 | − + + + + − + − + | 4257 | 2724 | 3491 | 0.31 | 589 |
| 20 | + + + + + + + + + | 1798 | 4923 | 3361 | 0.66 | 601 |

TABLE 11

Acidic DoE results.

| Run | Pattern | #1 (pg/mL) | #2 (pg/mL) | Mittelwert (pg/mL) | CV (%) | Relative Enzymaktivität (%) |
|---|---|---|---|---|---|---|
| | Kontrolle (25° C.) | 593 | 593 | 593 | 0 | 100 |
| | Kontrolle (37° C.) | 619 | 499 | 559 | 0.15 | 100 |
| 1 | + − + − + − − − − | −31 | −233 | −132 | −1.08 | −24 |
| 2 | + − − − − + + − − | 466 | 1553 | 1010 | 0.76 | 181 |
| 3 | − + − + − − − − + | −2 | 0 | −1 | −1.41 | 0 |
| 4 | − + − − − − + + − | 7051 | 4306 | 5679 | 0.34 | 958 |
| 5 | − − + + − − + − − | 123 | 111 | 117 | 0.07 | 20 |
| 6 | − − − + + − − + − | 20 | 28 | 24 | 0.24 | 4 |
| 7 | − − − − + + − − + | 91 | 27 | 59 | 0.77 | 10 |
| 8 | + + − + − + − − − | 332 | 362 | 347 | 0.06 | 62 |
| 9 | + − + − − − − + + | −95 | 132 | 19 | 8.68 | 3 |
| 10 | − + + − − + − − + | 847 | 111 | 479 | 1.09 | 81 |
| 11 | + + + − + − + − − | 612 | 1029 | 821 | 0.36 | 147 |
| 12 | + + − − + − − + + | 0 | 344 | 172 | 1.41 | 31 |
| 13 | + − − + − − + + + | −757 | 2393 | 818 | 2.72 | 146 |
| 14 | − + − − + + + + − | 1228 | 122 | 675 | 1.16 | 114 |
| 15 | − − + + + + − + − | 13 | 26 | 20 | 0.47 | 3 |
| 16 | − − + − − + + + + | 1170 | 674 | 922 | 0.38 | 155 |
| 17 | + + + + − + − + − | −12 | −11 | −12 | −0.06 | −2 |
| 18 | + − − + + + + − + | −149 | −176 | −163 | −0.12 | −29 |
| 19 | − + + + + − + − + | 1728 | 2037 | 1883 | 0.12 | 317 |
| 20 | + + + + + + + + + | 256 | 691 | 474 | 0.65 | 85 |

Example 2—Comparative Example

LEAP Assay

A non-limiting example for measuring, determining or quantifying hydrolase/hydrolase activity (hydrolytic activity) is an assay to detect lipolytic activity or, in other words, a lipase activity assay (e.g. as described by Jahn et al.), herein also termed LEAP (lipase enzymatic assay for polysorbates) assay (Jahn (2020) Pharm. Res. 37: 118).

This assay allow measuring, determining or quantifying hydrolase/hydrolase activity (hydrolytic activity) is a lipase activity assay (or in other words an assay to detect lipolytic activity) measuring the conversion of 4-methylumbelliferone caprylate (4 -MUCA) to 4-methylumbelliferone (4-MU). An assay using 4-MUCA as a substrate may be performed as described in the following.

10 μL of the composition comprising the protein in which hydrolase/hydrolase activity (hydrolytic activity) is to be determined may be mixed with 80 μL of reaction buffer (150 mM Tris-HCl pH 8.0, 0.25% (w/v) Triton X-100 and 0.125% (w/v) Gum Arabic) and 10 μL 4-MUCA substrate (1 mM in DMSO). The reactions may be set up in 96-well half-area polystyrene plates (black with lid and clear flat bottom, Corning Incorporated) and the increase of fluorescent signal (excitation at 355 nm, emission at 460 nm) may be monitored every 10 min by incubating the reaction plate for two hours at 37° C. for example in an Infinite 200Pro plate reader (Tecan Life Sciences) to derive the 4-MU production rate. The 4-MU production rate of the composition comprising the protein may be compared with the starting composition comprising a protein.

Example 3—Comparative Example

FAMS Assay

The following paragraph describes an exemplary sample preparation and analytical procedure for performing a FAMS assay.

The FAMS assay measures the lipase activity by quantifying the accumulation of free fatty acids through the hydrolysis of Polysorbate 20.

All samples (antibody solutions and buffer controls) may be supplemented with a stock solution of 1% (w/v) super-refined Polysorbate 20 (Croda Health Care) and 0.25 ML-Methionine (Sigma Aldrich, Art. No. M5308) to obtain a final concentration per sample of 0.04% (w/v) super-refined Polysorbate 20 and 0.01 M L-Methionine. For each spiked sample, aliquots of 190 μL may be transferred in five capped glass vials (termed t0, t1, t2, t3, t4), which may be used for sample incubation. The glass vials t0 may be frozen immediately at −70° C. after their preparation until analysis. The glass vials t1, t2, t3 and t4 may be incubated at 25° C. upright and protected from light in an incubator. Incubation of the glass vials may be stopped one at a time over a time period between the next five day and 14 days the glass vials may be subsequently frozen at −70° C. until analysis.

For analysis, frozen samples may be brought to ambient temperature for 1 hour. Stock solutions of stable isotope labelled fatty acids may be prepared by dissolving 50 mg of the respective fatty acid, lauric acid $^{2}d_{23}$ (Sigma Aldrich, Cat. No. 451401) and myristic acid $^{13}C_{14}$ (Sigma Aldrich, Cat. No. 605689) in 50 mL 80% acetone/20% methanol to obtain the precipitation reagent with a final concentration of 1 μg/mL for each investigated fatty acid. 50 μL of the sample solution may be added to 200 μL of the precipitation reagent in a reaction tube, mixed by vortexing and kept by room temperature for 1 h to allow the protein to precipitate. The precipitate may be spun down by centrifugation at 20° C. with 15,000×g for 15 min. 100 μL of the supernatant may be transferred in a fresh reaction tube and mixed with 100 μL of Mobile phase A (20 mM ammonium acetate). After spinning down at 20° C. with 15,000×g for 15 min, 50-100 μL of the solution may be transferred into LC-MS vials (300 μL Fixed Insert Vial (Clear, Screw Top), Thermo Scientific, Cat. No. 03-FISV).

Separation of fee fatty acids (FFAs) may be achieved on an ACQUITY UPLCH-Class System (Waters Corp. Milford, MA, US) equipped with a temperature-controllable auto sampler and column compartment by using a Jupiter® C4 RP column (300 Angstroms, 2×50 mm, 5 μm) (Phenomenex, Cat. No. 00B-4167-BO). Mobile Phase A may be 20 mM ammonium acetate (Sigma Aldrich, Cat. No. 73594) and Mobile Phase B may be 100% methanol (Merck, Cat. No. 1.06007.2500), which may be rum for 4 min. at a flow rate of 0.4 mL/min. by applying the following gradient: initial conditions: 70% Mobile Phase B, 0.5 min-3.4 min: gradient may be changed linearly from 70% to 85% Mobile Phase B; 3.5-4.0 min: 70% Mobile Phase B. The auto sampler may be maintained at 20° C. and the column compartment at 60° C. The injection volume may be set to 8 μL. Detection may be performed on a connected QDa Performance mass spectrometer (Waters) equipped with an external backing pump in negative ion mode. The MS settings may be as follows, cone voltage 15 V, source temperature 120° C., capillary voltage 800 V, probe temperature 600° C., mass range 50-1000 m/z and sampling frequency 2 Hz. All samples may be analyzed in triplicates.

Data evaluation may be performed with Target Lynx as part of the Mass Lynx Software Version 4.1 (SCN781) (Waters Corp. Milford, MA, US). The content of lauric and myristic acid may be determined by comparing the peak area of the fatty acid with the respective internal labelled standard by using the following formula (3):

$$Conc.(FFA) = \frac{\sum \text{Peak areas of } FFA}{\sum \text{Peak areas of Internal standard}} * 4 * 1\ \mu g/\text{mL} \tag{3}$$

where ΣPeak areas of FFA and ΣPeak areas of Internal standard refer to the sum of the monoisotopic peak and the isotopic peaks at +1/+2 or −1/−2, respectively.

For determining the fatty acid release rate, the free fatty acid concentration for each sample may be plotted against the incubation time and the degradation may be extracted from the slope of the linear regression

Example 4

Assay According to the Invention

An exemplary method including sample preparation and its measurement for performing an Elecsys based Polysorbase Activity (EPA) assay according to the current invention is presented in this Example.

EPA assay determines hydrolase/hydrolase activity (hydrolytic activity) in samples. The source or matrix of the sample does not influence the EPA. Thus, samples from various different stages of purification (from HCCF until UFDF pool) can be analyzed.

Figure 4:
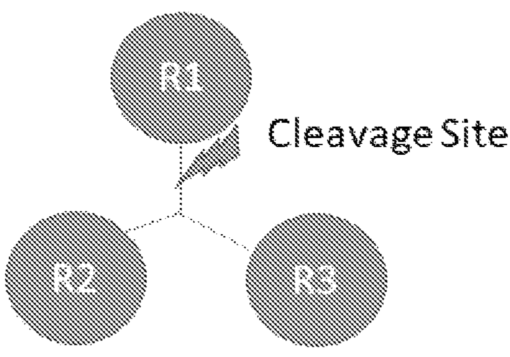
FIG. 4 Schematic representation of the chemical structure of the artificial substrate according to the invention with three different residues. R3 is an antigen of a specific cardenolide, e.g. digoxygenin. R2 is a class of high-affinity RNA analogues and R1 is part of a non-covalent, biological binding pair, e.g. biotin (biotin/avidin pair)). The thunder-like arrow shows an ester bond. Hydrolytically active HCPs cleave this ester bond, as result of which an alcohol and an acid are released from the substrate.
Figure 5:
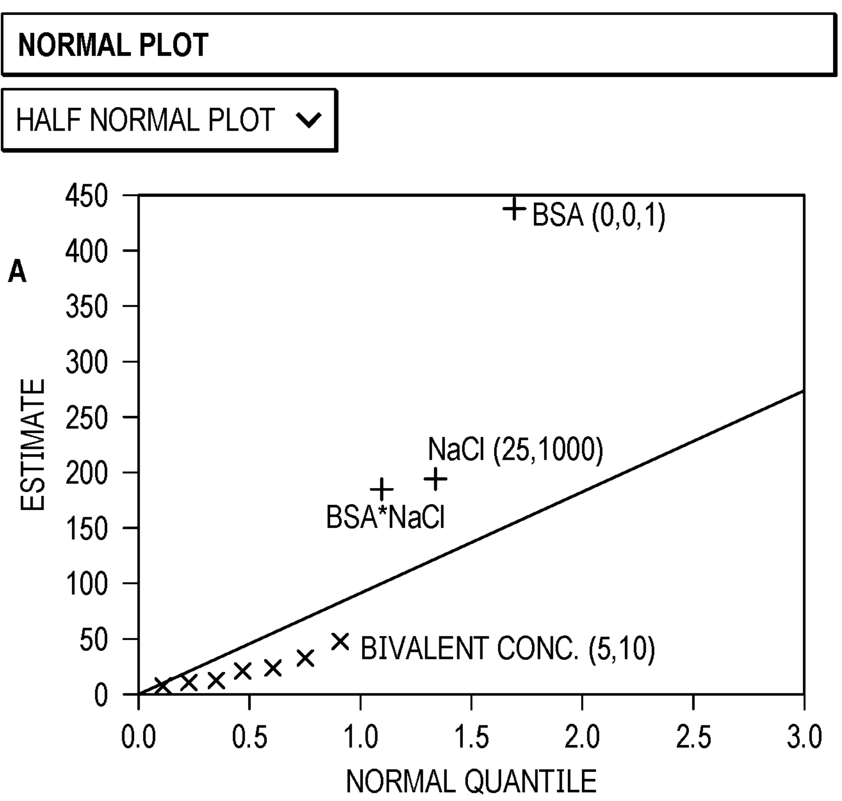
FIG. 5 Graphical representation of the factors tested for influence on the enzyme activity. (A) Half-normal probability plot. (B) Pareto plot.
Figure 5:
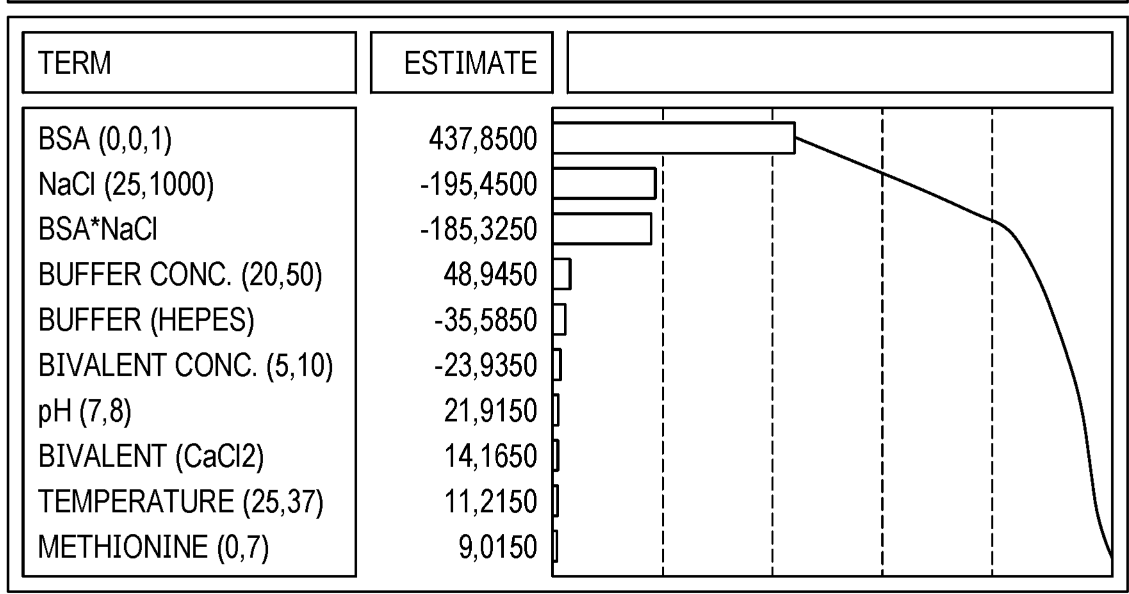
Figure 6:
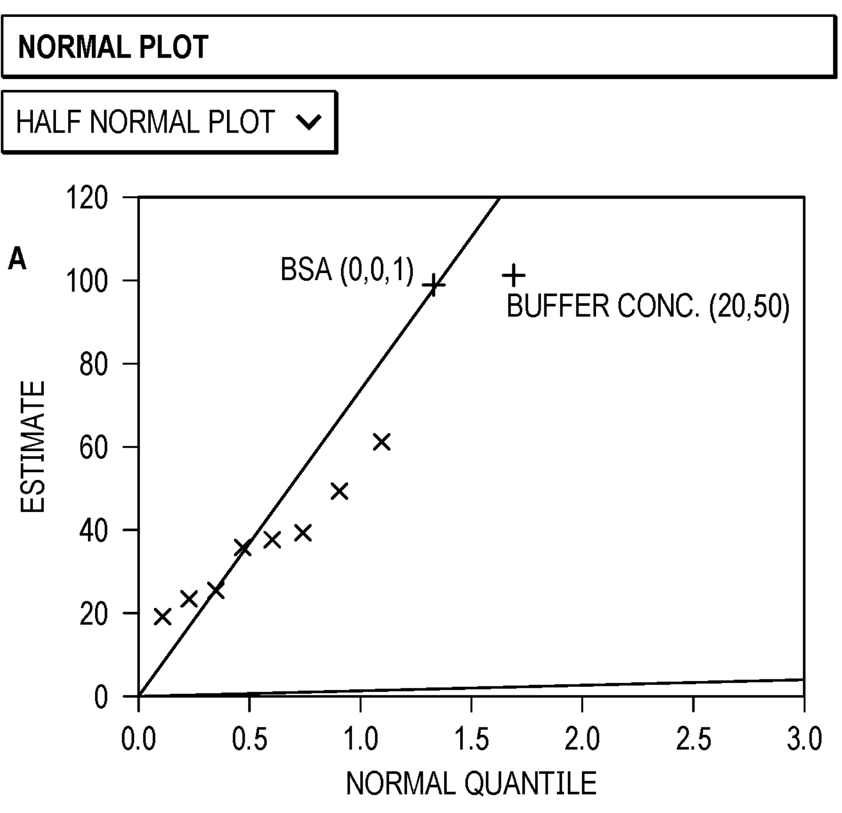
FIG. 6 Graphical representation of the factors tested for influence on the enzyme activity in the pH range between pH 6-7. (A) Half-normal probability plot. (B) Pareto plot.
Figure 6:
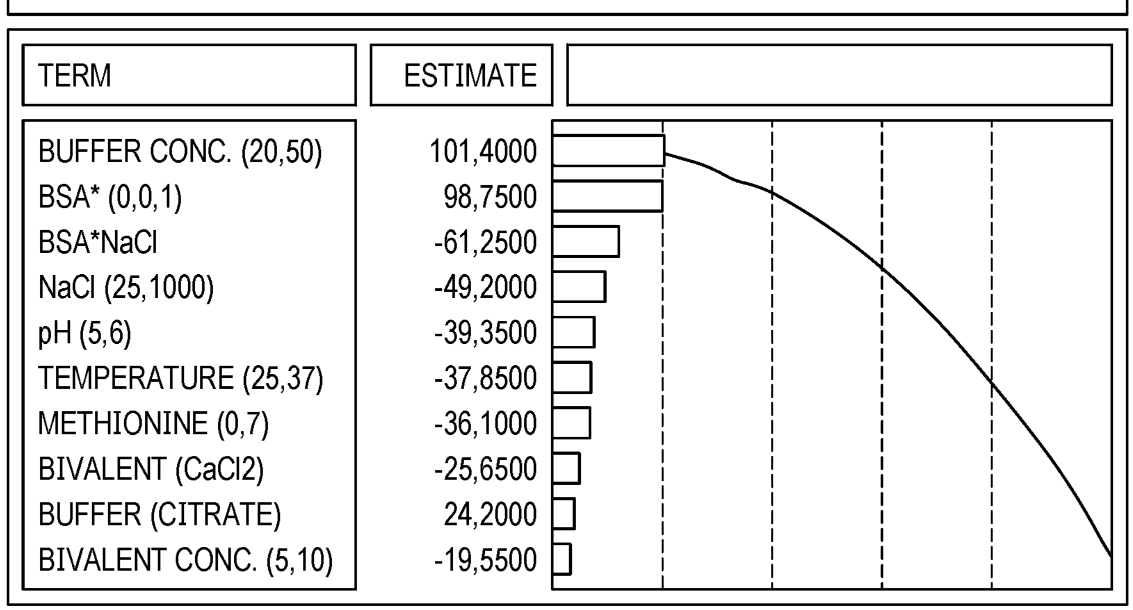
Figure 7:
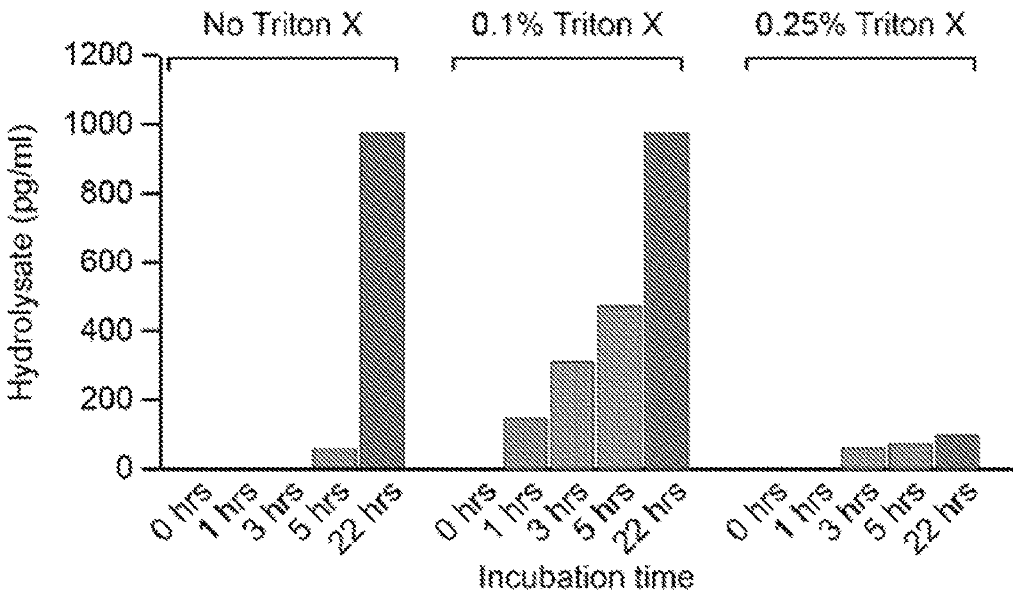
FIG. 7 Graphic representation of the detergent effect.
Figure 8:
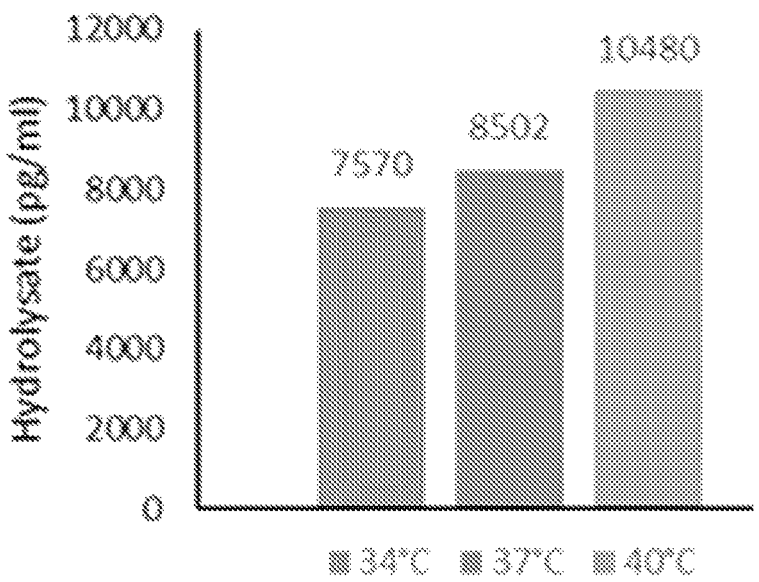
FIG. 8 Effect of temperature on the method according to the invention.
Figure 9:
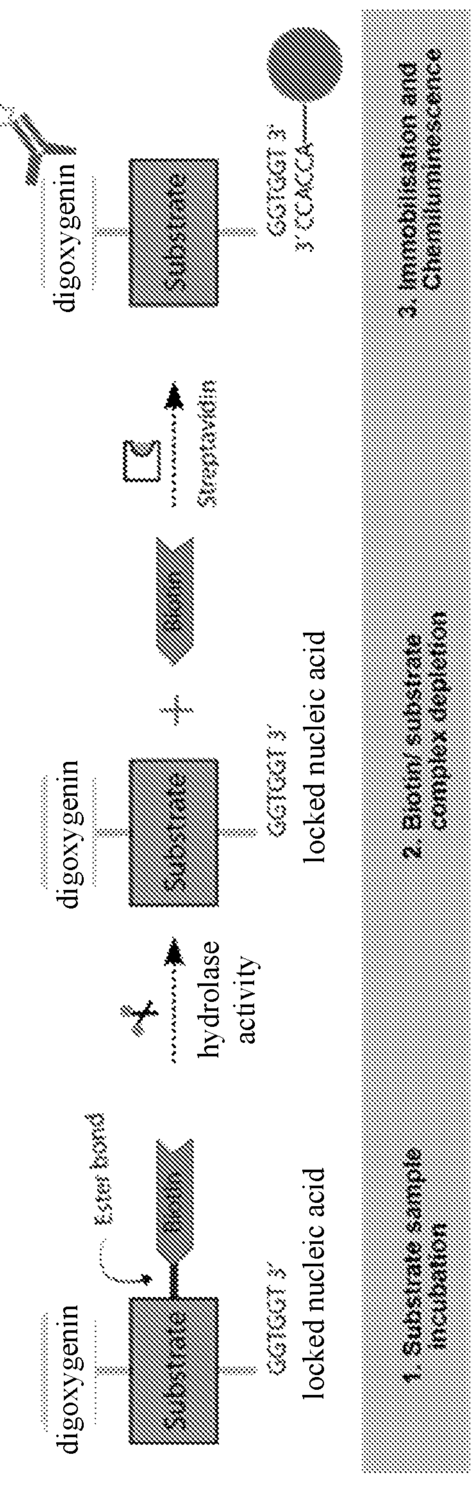
FIG. 9 Scheme of an exemplary assay according to the invention.
Figure 10:
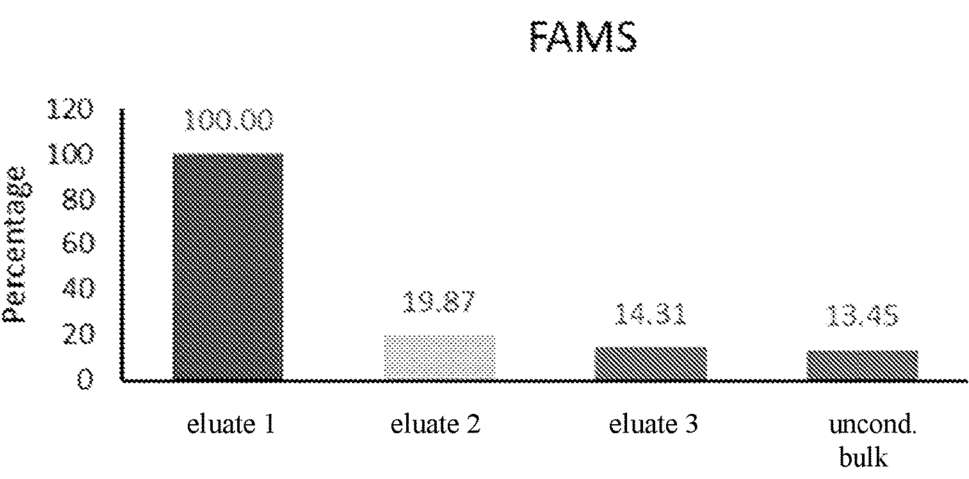
FIG. 10 Bar graph of percent error for FAMS assay for in process samples of exemplary therapeutic polypeptide 3.
Figure 11:
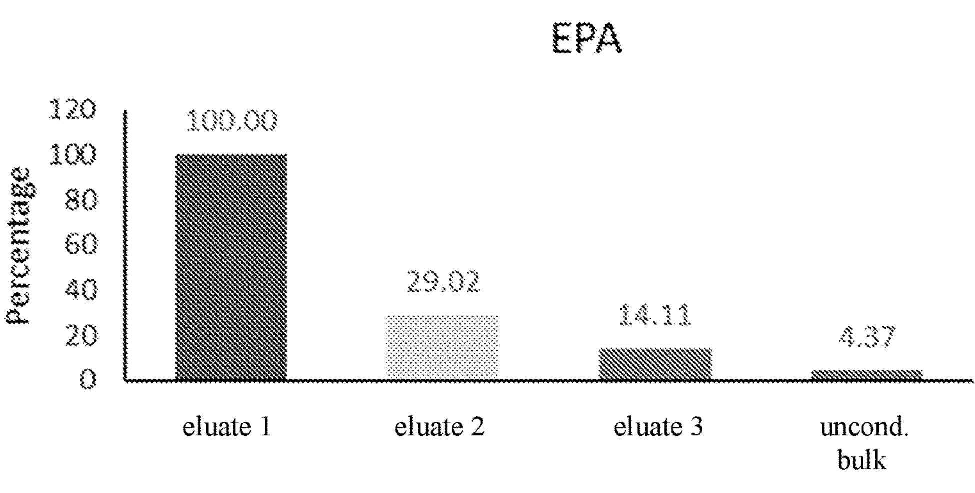
FIG. 11 Bar graph of percent error for the method according to the invention for in process samples of exemplary therapeutic polypeptide 3.
Figure 12:
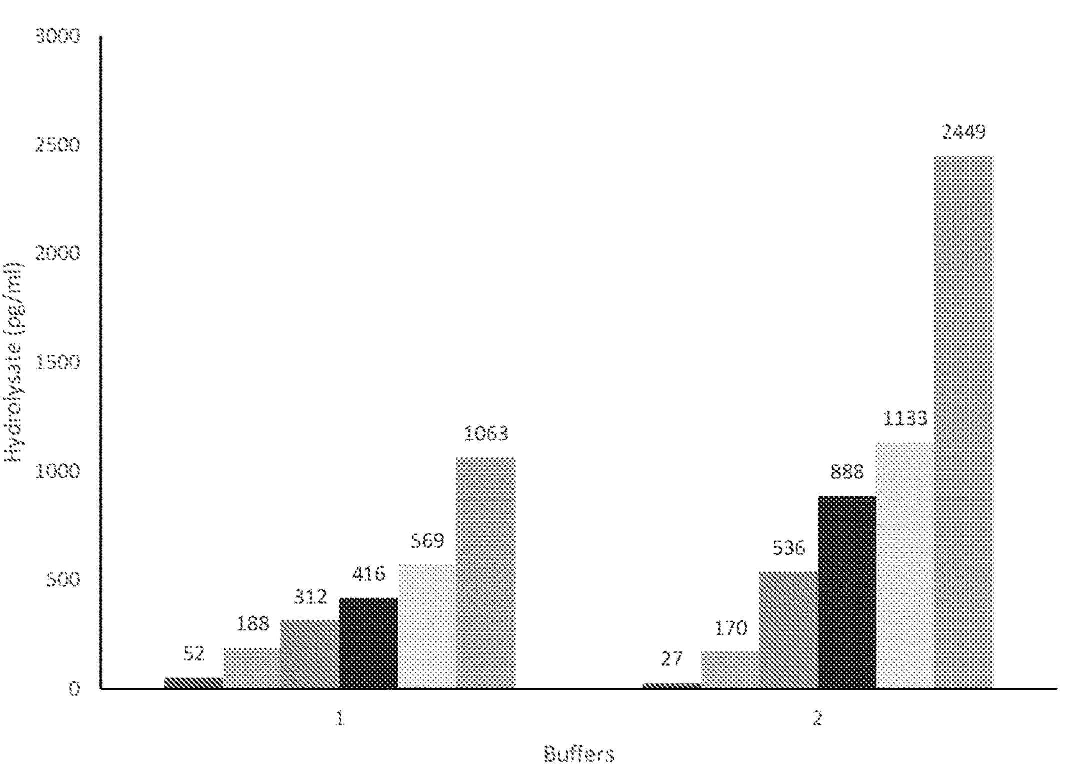
FIG. 12 Bar graph showing the amount of generated hydrolysate in a method according to the current invention depending on the employed buffer: TRIS-based buffer on the left, MOPS-based buffer on the right.
Figure 13:
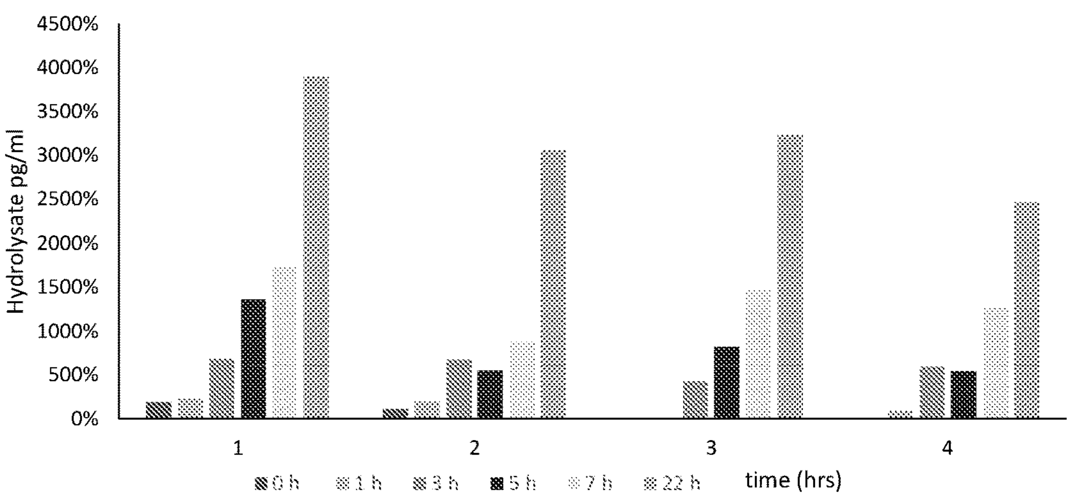
FIG. 13 Effect of BSA and various grades of BSA on the method according to the current invention.

An artificial hydrolase substrate according to the invention (FIG. 4) is used in this Example comprising:

1) A biotin moiety as R1, coupled via an ester bond, which is susceptible to cleavage by hydrolases present in samples;
2) L-Locked Nucleic Acid (LNA) as R2, used for immobilization of the cleaved substrate onto a solid surface;
3) Digoxygenin as R3, used for detection of immobilized cleaved substrate using Ruthenium labeled anti-digoxygenin antibody.

Sample and analysis buffer are mixed to obtain a mixture comprising final concentrations of 150 mM MOPS, 5 mM $MgCl_2$, 6 μM BSA, 25 mM NaCl, 0.1% (w/v) Triton X-100 and 0.1-250 mg/mL protein at a pH value of 7. This reaction mixture is incubated at 37° C. for the respective time, i.e. 1, 3, 5, 7, 22 or 48 hours.

A standard EPA reaction is performed in duplicates where the substrate is incubated with samples (antibody solutions and buffer controls) to be measured for various time points (up to 48 hours).

In next steps, the digested biotin moieties along with undigested substrate is removed from the reaction mix using magnetic Streptavidin beads (Cytiva, Art. No. 28985799) according to the manufacturer's instructions.

The corresponding duplicates are combined (pooled) and the content of released alcohol part of the artificial hydrolase substrate is determined using L-LNA capture and Digoxygenin determination (as a readout) on a Cobas e411 analyzer according to the manufacturer's instructions. The readout is the amount of hydrolysate (in pg) detected per ml sample.

The amount of hydrolysate detected (pg/ml) in the corresponding sample is corrected for the amount of hydrolysate detected (pg/ml) in a blank sample (using e.g. water instead of the protein sample) according to equation (3).

$$\text{Blank corrected value} = \text{hydrolysate detected in sample (pg/ml)} - \text{hydrolysate detected in blank (pg/ml)} \tag{3}$$

The blank corrected value for each sample is normalized to its protein concentration, giving a final readout in pg of hydrolysate detected per mg of protein according to equation (4):

$$\text{Normalized hydrolytic activity (pg/ml)} = \text{Blank corrected value (pg/mL)} * 1000\ \text{mL}/\text{protein per well } (\mu g) \tag{4}$$

To calculate the rate at which hydrolases present in a sample digest the artificial hydrolase substrate, rate of hydrolysis is determined and is represented in pg of hydrolysate detected per mg of protein per hour according to equation (5):

$$\text{Rate of hydrolysis }(\text{pg/mg}/h) = \text{normalized activity }(\text{pg/mg})/\text{incubation time }(h) \quad (5)$$

The invention claimed is:

1. A method for determining hydrolase activity in a sample, wherein the hydrolase is an esterase capable of hydrolysis of carboxylic acid esters producing an alcohol and a carboxylic acid, the method comprising the following steps:

a) incubating the sample or an aliquot thereof and a buffered solution to form an incubated sample, wherein the buffered solution comprises a buffer substance, an artificial hydrolase substrate, a salt and bovine serum albumin, wherein the sample comprises a therapeutic polypeptide, wherein the artificial hydrolase substrate comprises a single ester bond covalently linking a carboxylic acid residue, which is conjugated to a first label, and an alcohol residue, which is conjugated to a nucleic acid tag and a second label, which is different from the first label, wherein the artificial hydrolase substrate is represented by the following formula:

R2,R3 [O ... ]$_n$ ... O C(=O) ... [O ... ]$_m$ R1 wherein, n and m each independently of each other is zero or a positive integer value, R1 comprises the first label, and R2, R3 comprises the second label and the nucleic acid tag, wherein the ester bond in the artificial hydrolase substrate is cleaved into a free alcohol residue and a free carboxylic acid residue if hydrolase activity and/or a hydrolase is present in the sample, b) removing the free carboxylic acid residue and artificial hydrolase substrate from the incubated sample to obtain a depleted sample, wherein the removing is carried out by contacting the incubated sample with a first solid phase, which specifically binds to the first label, and separating the free carboxylic acid and artificial hydrolase substrate-depleted incubation mixture from the first solid phase thereafter, c) determining hydrolase activity and/or the presence of a hydrolase in the sample by determining the second label in the depleted sample, wherein the determining is carried out by capturing the free alcohol residue on a second solid phase via the nucleic acid tag followed by detecting the solid-phase captured free alcohol residue with an antibody specifically binding to the second label, which antibody is conjugated to one or more detectable labels.

2. The method according to claim 1, wherein the detection is with an electrochemiluminescense immunoassay and the second label is a ruthenium label.

3. The method according to claim 1, wherein the detection is with an antibody specifically binding to the second label, wherein the antibody is conjugated to one or more ruthenium labels.

4. The method according to claim 2 or claim 3, wherein the ruthenium label is a detectable ruthenium label.

5. The method according to claim 1, wherein the first and the second label are selected independently of each other from the group of specific binding pairs.

6. The method according to claim 1, wherein the nucleic acid tag is a locked nucleic acid.

7. The method according to claim 1, wherein the nucleic acid tag has the sequence in 3' to 5'-direction TGGTTG.

8. The method according to claim 1, wherein the alcohol of the artificial hydrolase substrate and the carboxylic acid of the artificial hydrolase substrate each comprises independently of each other one or more ethylene oxide ($CH_2$—$CH_2$—O) units.

9. The method according to claim 1, wherein the buffered solution has a pH value of about 7.

10. The method according to claim 1, wherein the incubating is at a temperature of about 37° C.

11. The method according to claim 1, wherein the incubating is for up to 22 hours.

12. The method according to claim 1, wherein the buffer solution comprises a final concentration of 3 μM to 10 μM bovine serum albumin.

13. The method according to claim 1, wherein the buffer solution comprises a final concentration of about 150 mM MOPS, about 5 mM $MgCl_2$, about 25 mM NaCl and about 6 μM Cys34 oxidized bovine serum albumin.

14. The method according to claim 1, wherein the first label is biotin or a variant thereof and the second label is digoxygenin or a variant thereof.

15. The method according to claim 1, wherein the buffer solution further comprises a final concentration of about 0.05% to 0.15% (w/v) of a detergent.

16. The method according to claim 15, wherein the detergent is Octoxinol-9.

* * * * *

SEQUENCE LISTING

```
Sequence total quantity: 46
SEQ ID NO: 1            moltype =   length =
SEQUENCE: 1
000

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000

SEQ ID NO: 11           moltype =   length =
SEQUENCE: 11
000

SEQ ID NO: 12           moltype =   length =
SEQUENCE: 12
000

SEQ ID NO: 13           moltype =   length =
SEQUENCE: 13
000

SEQ ID NO: 14           moltype =   length =
SEQUENCE: 14
000

SEQ ID NO: 15           moltype =   length =
SEQUENCE: 15
000

SEQ ID NO: 16           moltype =   length =
SEQUENCE: 16
000

SEQ ID NO: 17           moltype = DNA  length = 12
FEATURE                 Location/Qualifiers
misc_feature            1..12
                        note = tag-17
source                  1..12
```

```
                        mol_type = other DNA
                        organism = synthetic construct
SEQUENCE: 17
caacacacca ac                                                12

SEQ ID NO: 18           moltype = DNA  length = 10
FEATURE                 Location/Qualifiers
misc_feature            1..10
                        note = tag-18
source                  1..10
                        mol_type = other DNA
                        organism = synthetic construct
SEQUENCE: 18
acacaccaac                                                   10

SEQ ID NO: 19           moltype =   length =
SEQUENCE: 19
000

SEQ ID NO: 20           moltype =   length =
SEQUENCE: 20
000

SEQ ID NO: 21           moltype =   length =
SEQUENCE: 21
000

SEQ ID NO: 22           moltype =   length =
SEQUENCE: 22
000

SEQ ID NO: 23           moltype = DNA  length = 12
FEATURE                 Location/Qualifiers
misc_feature            1..12
                        note = tag-23
source                  1..12
                        mol_type = other DNA
                        organism = synthetic construct
SEQUENCE: 23
gttggtgtgt tg                                                12

SEQ ID NO: 24           moltype =   length =
SEQUENCE: 24
000

SEQ ID NO: 25           moltype =   length =
SEQUENCE: 25
000

SEQ ID NO: 26           moltype =   length =
SEQUENCE: 26
000

SEQ ID NO: 27           moltype =   length =
SEQUENCE: 27
000

SEQ ID NO: 28           moltype =   length =
SEQUENCE: 28
000

SEQ ID NO: 29           moltype =   length =
SEQUENCE: 29
000

SEQ ID NO: 30           moltype =   length =
SEQUENCE: 30
000

SEQ ID NO: 31           moltype = DNA  length = 15
FEATURE                 Location/Qualifiers
misc_feature            1..15
                        note = tag-31
source                  1..15
                        mol_type = other DNA
                        organism = synthetic construct
SEQUENCE: 31
gttggtgtgt tggtg                                             15
```

```
SEQ ID NO: 32           moltype = DNA  length = 15
FEATURE                 Location/Qualifiers
misc_feature            1..15
                        note = tag-32
source                  1..15
                        mol_type = other DNA
                        organism = synthetic construct
SEQUENCE: 32
caccaacaca ccaac                                                             15

SEQ ID NO: 33           moltype =   length =
SEQUENCE: 33
000

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000

SEQ ID NO: 38           moltype =   length =
SEQUENCE: 38
000

SEQ ID NO: 39           moltype =   length =
SEQUENCE: 39
000

SEQ ID NO: 40           moltype =   length =
SEQUENCE: 40
000

SEQ ID NO: 41           moltype =   length =
SEQUENCE: 41
000

SEQ ID NO: 42           moltype =   length =
SEQUENCE: 42
000

SEQ ID NO: 43           moltype =   length =
SEQUENCE: 43
000

SEQ ID NO: 44           moltype =   length =
SEQUENCE: 44
000

SEQ ID NO: 45           moltype =   length =
SEQUENCE: 45
000

SEQ ID NO: 46           moltype =   length =
SEQUENCE: 46
000
```